(12) United States Patent
Zbrzeski et al.

(10) Patent No.: US 9,662,025 B2
(45) Date of Patent: May 30, 2017

(54) LOW NOISE ANALOG ELECTRONIC CIRCUIT DESIGN FOR RECORDING PERIPHERAL NERVE ACTIVITY

(71) Applicant: THE FLORIDA INTERNATIONAL UNIVERSITY BOARD OF TRUSTEES, Miami, FL (US)

(72) Inventors: Adeline Zbrzeski, Miami, FL (US); Ranu Jung, Miami Beach, FL (US)

(73) Assignee: The Florida International University Board of Trustees, Miami, FL (US)

( * ) Notice: Subject to any disclaimer, the term of this patent is extended or adjusted under 35 U.S.C. 154(b) by 371 days.

(21) Appl. No.: 13/886,934

(22) Filed: May 3, 2013

(65) Prior Publication Data

US 2014/0330102 A1 Nov. 6, 2014

(51) Int. Cl.
 A61B 5/04 (2006.01)
 H03F 3/45 (2006.01)
 A61B 5/00 (2006.01)

(52) U.S. Cl.
 CPC ........ *A61B 5/04001* (2013.01); *A61B 5/7225* (2013.01); *H03F 3/45179* (2013.01); *H03F 3/45475* (2013.01); *H03F 2200/261* (2013.01); *H03F 2203/45138* (2013.01)

(58) Field of Classification Search
 CPC .............. A61B 5/04001; A61B 5/7225; H03F 3/45179; H03F 3/45475; H03F 3/45138
 See application file for complete search history.

(56) References Cited

U.S. PATENT DOCUMENTS

| 4,088,962 | A | * | 5/1978 | Trilling | ............... | H03F 3/45085 |
| | | | | | | 330/103 |
| 4,766,394 | A | * | 8/1988 | Yukawa | ................ | H03F 3/3028 |
| | | | | | | 330/253 |
| 5,831,542 | A | * | 11/1998 | Thomas | ................. | A01C 7/105 |
| | | | | | | 310/345 |
| 6,262,628 | B1 | * | 7/2001 | Shinomiya | .......... | H03F 3/45089 |
| | | | | | | 330/252 |
| 7,688,140 | B2 | * | 3/2010 | Yuasa | .................... | H03F 3/3022 |
| | | | | | | 330/252 |
| 2003/0207679 | A1 | * | 11/2003 | Kaczynski | ......... | H03H 11/0433 |
| | | | | | | 455/339 |
| 2006/0007221 | A1 | * | 1/2006 | Eaton | ..................... | H04N 17/04 |
| | | | | | | 345/207 |
| 2006/0119429 | A1 | * | 6/2006 | Lim | ........................ | H03F 3/189 |
| | | | | | | 330/253 |

(Continued)

OTHER PUBLICATIONS

Arnaud, A. et al., "Nanowatt, Sub-ns. OTAs With Sub-10mV Input Offset, Using Series Parallel Current Mirrors," *IEEE Journal of Solid-State Circuits*, Sep. 2006, vol. 41, Issue 9, p. 2009-2018.

(Continued)

*Primary Examiner* — Michael C Stout
(74) *Attorney, Agent, or Firm* — Saliwanchik, Lloyd & Eisenschenk

(57) ABSTRACT

Circuits and circuit systems to record activity (e.g., peripheral nerve activity) are provided. The circuits advantageously have good noise characteristics (e.g., low noise), as well as low power consumption and low area. A circuit can be implantable (e.g., in a human subject). Methods of designing, manufacturing, and using such circuits and circuit systems are also provided.

23 Claims, 8 Drawing Sheets

(56) References Cited

U.S. PATENT DOCUMENTS

| | | | | |
|---|---|---|---|---|
| 2007/0096799 | A1* | 5/2007 | Marais | H03H 11/04 327/557 |
| 2008/0077039 | A1* | 3/2008 | Donnett | A61B 5/0006 600/544 |
| 2008/0290944 | A1* | 11/2008 | Sarpeshkar | H03F 1/0266 330/261 |
| 2009/0082691 | A1* | 3/2009 | Denison | A61B 5/04004 600/544 |
| 2009/0115516 | A1* | 5/2009 | Park | H03F 3/45183 330/253 |
| 2009/0171236 | A1* | 7/2009 | Davies | A61B 5/0537 600/547 |
| 2010/0036211 | A1* | 2/2010 | La Rue | A61B 5/0002 600/301 |
| 2010/0274114 | A1* | 10/2010 | Denker | A61B 5/04012 600/373 |
| 2011/0061947 | A1* | 3/2011 | Krah | G06F 1/3215 178/18.01 |
| 2011/0092834 | A1* | 4/2011 | Yazicioglu | A61B 5/0402 600/509 |
| 2012/0044021 | A1* | 2/2012 | Yeh | H03F 1/0205 330/257 |
| 2013/0116577 | A1* | 5/2013 | Yazicioglu | A61B 5/04017 600/483 |
| 2013/0169361 | A1* | 7/2013 | Killat | H03F 3/45183 330/253 |
| 2013/0237874 | A1* | 9/2013 | Zoicas | A61B 5/0452 600/521 |
| 2013/0307623 | A1* | 11/2013 | Dusad | H03F 3/45 330/261 |

OTHER PUBLICATIONS

Azin, M. et al., "A Battery-Powered Activity-Dependent Intracortical Microstimulation IC for Brain-Machine-Brain Interface," *IEEE Journal of Solid-State Circuits*, Apr. 2011, vol. 46, Issue 4, p. 731-745.

Branner, A. et al., "Mutlielectrode Array for Intrafascicular Recording and Stimulation in Sciatic Nerve of Cats," *Brain Research Bulletin*, Mar. 2000, vol. 51, No. 4, p. 293-306.

Branner, A. et al., "Long-Term Stimulation and Recording With a Penetrating Microelectrode Array in Cat Sciatic Nerve," *IEEE Transactions on Biomedical Engineering*, Jan. 2004, vol. 51, No. 1, p. 146-157.

Campbell, P. et al., "A Silicon-Based, Three-Dimensional Neural Interface: Manufacturing Processes for an Intracortical Electrode Array," *IEEE Transactions on Biomedical Engineering*, Aug. 1991, vol. 38, No. 8, p. 758-768.

Chen, WM.et al., "The Design of CMOS General-Purpose Analog Front-End Circuit with Tunable Gain and Bandwidth for Biopotential Signal Recording Systems, Engineering in Medicine and Biology Society," *EMBC, Annual International Conference of the IEEE*, Sep. 2011, p. 4784-4787.

Dagetkin, M. et al., "A Multi Channel Chopper Modulated Neural Recording System, Engineering in Medicine and Biology Society," *Proceedings of the 23rd Annual International Conference of the IEEE*, 2001, p. 1-5.

Denison, T. et al., "A 2 μW 100 nV/rtHz Chopper-Stabilized Instrumentation Amplifier for Chronic Measurement of Neural Field Potentials," *IEEE Journal of Solid-State Circuits*, Dec. 2007, vol. 42, No. 12, p. 2934-2945.

Dhillon, G. et al., "Direct Neural Sensory Feedback and Control of a Prosthetic Arm," *IEEE Transactions on Neural Systems and Rehabilitation Engineering*, Dec. 2005, vol. 13, No. 4, p. 468-472.

Dhillon, G. et al., "Effects of Short-Term Training on Sensory and Motor Function in Severed Nerves of Long-Term Human Amputees," *Journal of Neurophysiology*, 2005, vol. 93, No. 5, p. 2625-2633.

Dhillon, G. et al., "Residual Function in Peripheral Nerve Stumps of Amputees: Implications for Neural Control of Artificial Limbs," *Journal of Hand Surgery*, Jul. 2004, vol. 29, No. 4, p. 605-615.

Edell, D., "A Peripheral Nerve Information Transducer for Amputees: Long-Term Multichannel Recordings from Rabbit Peripheral Nerves," *IEEE Transactions on Biomedical Engineering*, Feb. 1986, vol. 33, No. 2, p. 203-214.

Figoni, S. et al., "Acute Hemodynamic Responses of Spinal Cord Injured Individuals to Functional Neuromuscular Stimulation-Induced Knee Extension Exercise," *Journal of Rehabilitation Research and Development*, Nov. 4, 1991, vol. 28, No. 4, p. 9-18.

Gibson, S. et al., "Technology-Aware Algorithm Design for Neural Spike Detection, Feature Extraction, and Dimensionality Reduction," *IEEE Transactions on Neural Systems and Rehabilitation Engineering*, Oct. 2010, vol. 18, No. 5, p. 469-478.

Goodall, E. et al., "Information Contained in Sensory Nerve Recordings Made with Intrafascicular Electrodes," *IEEE Transactions on Biomedical Engineering*, Sep. 1991, vol. 38, No. 9, p. 846-850.

Goodall, E. et al., "Separation of Action Potentials in Multiunit Intrafascicular Recordings," *IEEE Transactions on Biomedical Engineering*, Mar. 1992, vol. 39, No. 3, p. 289-295.

Grill, W., "Electrical Activation of Spinal Neural Circuits: Application to Motor-System Neural Prostheses," *Neuromodulation*, 2000, vol. 3, No. 2, p. 97-106.

Hallin, R., "Microneurography in Relation to Intraneural Topography: Somatotopic Organisation of Median Nerve Fascicles in Humans," *Journal of Neurology, Neurosurgery, and Psychiatry*, 1990, vol. 53, No. 9, p. 736-744.

Hallin, R. et al., "Fitting Pieces in the Peripheral Nerve Puzzle," *Experimental Neurology*, 2001, vol. 172, No. 2, p. 482-492.

Harrison, R., "The Design of Integrated Circuits to Observe Brain Activity," *Proceedings of the IEEE*, Jul. 2008, vol. 96, No. 7, p. 1203-1216.

Harrison, R. et al., "A Low-Power Low-Noise CMOS Amplifier for Neural Recording Applications," *IEEE Journal of Solid-State Circuits*, Jun. 2003, vol. 38, No. 6, p. 958-965.

Jensen, W. etal., "Improving Signal Reliability for On-Line Joint Angle Estimation From Nerve Cuff Recordings of Muscle Afferents," *IEEE Transactions on Neural Systems and Rehabilitation Engineering*, Sep. 2002, vol. 10, No. 3, p. 133-139.

Keith, M., "Neuroprostheses for the Upper Extremity," *Microsurgery*, 2001, vol. 21, No. 6, p. 256-263.

Kovacs, G. et al., "Regeneration Microelectrode Array for Peripheral Nerve Recording and Stimulation," *IEEE Transactions on Biomedical Engineering*, Sep. 1992, vol. 39, No. 9, p. 893-902.

Kim, K. et al., "Neural Spike Sorting Under Nearly 0-dB Signal-to-Noise Ratio Using Nonlinear Energy Operator and Artificial Neural-Network Classifier," *IEEE Transactions on Biomedical Engineering*, Oct. 2000, vol. 47, No. 10, p. 1406-1411.

Lee, J. et al., "A Tunable Biquad Switched-Capacitor Amplifier-Filter for Neural Recording," *IEEE Transactions on Biomedical Circuits and Systems*, Oct. 2010, vol. 4, No. 5, p. 295-300.

Lee, S. et al., "An Inductively Powered Scalable 32-Channel Wireless Neural Recording Systemon-a-Chip for Neuroscience Applications," *IEEE Transactions on Biomedical Circuits and Systems*, Dec. 2010, vol. 4, No. 6, p. 360-371.

Lefurge, T. et al., "Chronically Implanted Intrafascicular Recording Electrodes," *Annals of Biomedical Engineering*, 1991, vol. 19, No. 2, p. 197-207.

Limnuson, K. et al., "Integrated Electronics for Peripheral Nerve Recording and Signal Processing," *Annual International Conference of the IEEE*, Sep. 2009, p. 1639-1642.

Lopez, C. et al., "A Multichannel Integrated Circuit for Electrical Recording of Neural Activity, with Independent Channel Programmability," *IEEE Transactions on Biomedical Circuits and Systems*, April, 101-110, vol. 6, No. 2, p. 101-110.

Majidzadeh, V. et al., "Energy Efficient Low-Noise Neural Recording Amplifier with Enhanced Noise Efficiency Factor," *IEEE Transactions on Biomedical Circuits and Systems*, Jun. 2011, vol. 5, No. 3, p. 262-271.

(56) References Cited

OTHER PUBLICATIONS

Malagodi, M. et al., "An Intrafascicular Electrode for Recording of Action Potentials in Peripheral Nerves," *Annals of Biomedical Engineering*, 1989, vol. 37, No. 4, p. 397-410.
Malmstrom, J. et al., "Recording Properties and Biocompatibility of Chronically Implanted Polymer-based Intrafascicular Electrodes," *Annals of Biomedical Engineering*, 1998, vol. 26, No. 6, p. 1055-1064.
McDonnall, M.et al., "Selective Motor Unit Recruitment via Intrafascicular Multielectrode Stimulation," *Canadian Journal of Physiology and Pharmacology*, 2004, vol. 82, p. 599-609.
McNaughton, T. etal., "Action Potential Classifier with Dual Channel Intrafascicular Electrodes," *IEEE Transactions on Biomedical Engineering*, Jul. 1994, vol. 41, No. 7, p. 609-616.
Mensinger, A. et al., "Chronic Recording of Regenerating VIIIth Nerve Axons with a Sieve Electrode," *Journal of Neurophysiology*, Jan. 2000, vol. 83. No. 1, p. 611-615.
Nabar, N. et al., "A Wavelet based Teager Energy Operator for Spike Detection in Microelectrode Array Recordings," *2009 IEEE Region 10 Conference*, TENCON 2009, p. 1-6.
Naples, G. et al., "A Spiral Nerve Cuff Electrode for Peripheral Nerve Stimulation," *IEEE Transactions on Biomedical Engineering*, Nov. 1988, vol. 35, No. 11, p. 905-916.
Navarro, X. et al., "Selective Fascicular Stimulation of the Rat Sciatic Nerve with Multipolar Polyimide Cuff Electrodes," *Restorative Neurology and Neuroscience*, 2001, vol. 18, No. 1, p. 9-21.
Nikolic, Z. et al., "Instrumentation for ENG and EMG Recordings in FES Systems," *IEEE Transactions on Biomedical Engineering*, Jul. 1994, vol. 41, No. 7, p. 703-706.
Obeid, I., "Comparison of Spike Detectors based on Simultaneous Intracellular and Extracellular Recordings," *Proceedings of the 3rd International IEEE EMBS Conference on Neural Engineering*, May 2007, p. 410-413.
Obeid, I. et al., "Evaluation of Spike-Detection Algorithms for a Brain-Machine Interface Application," *IEEE Transactions on Biomedical Engineering*, Jun. 2004, vol. 51, No. 6, p. 905-911.
Ohnishi, K. et al., "Neural Machine Interfaces for Controlling Multifunctional Powered Upper-limb Prostheses," *Expert Review of Medical Devices*, 2007, vol. 4, No. 1, p. 43-53.
Rezaee-Dehsorkh, H. et al., "Analysis and Design of Tunable Amplifiers for Implantable Neural Recording Applications," *IEEE Journal on Emerging and Selected Topics in Circuits and Systems*, Dec. 2011, vol. 1, No. 4, p. 546-556.
Rieger, R., "Variable-Gain, Low-Noise Amplification for Sampling Front Ends," *IEEE Transactions on Biomedical Circuits and Systems*, Jun. 2011, vol. 5, No. 3, p. 253-261.
Rossini, P. et al., "Stump Nerve Signals During Transcranial Magnetic Motor Cortex Stimulation Recorded in an Amputee via Longitudinal Intrafascicular Electrodes," *Experimental Brain Research*, Mar. 2011, vol. 210, No. 1, p. 1-11.
Shalchyan, V. et al., "Spike Detection and Clustering with Unsupervised Wavelet Optimization in Extracellular Neural Recordings," *IEEE Transactions on Biomedical Engineering*, Sep. 2012, vol. 59, No. 9, p. 2576-2585.
Stein, R. et al., "Principles Underlying New Methods for Chronic Neural Recording," *Canadian Journal of Neurological Science*, 1975, vol. 2, No. 3, p. 235-244.
Stein, R. et al., "Stable Long-term Recordings from Cat Peripheral Nerves," *Brain Research*, 1977, vol. 128, No. 1, p. 21-38.
Sweeney, J. et al., "Neuromuscular Stimulation Selectivity of Multiple-contact Nerve Cuff Electrode Arrays," *Medical and Biological Engineering and Computing*, 1995, vol. 33, p. 418-425.
Upshaw, B. et al., "Digital Signal Processing Algorithms for the Detection of Afferent Nerve Activity Recorded from Cuff Electrodes," *IEEE Transactions on Rehabilitation Engineering*, Jun. 1998, vol. 6, No. 2, p. 172-181.
Uranga, A. et al., "Integrated CMOS Amplifier for ENG Signal Recording," *IEEE Transactions on Biomedical Engineering*, Dec. 2004, vol. 51, No. 12, p. 2188-2194.
Venkatasubramanian G. et al., "Functional Electrical Stimulation," *The Wiley Encyclopedia of Medical Devices and Instrumentation*, 2006, J.G. Webster, Wiley-Interscience.
Watchmaker, G. et al., "Fascicular Topography of the Median Nerve: A Computer Based Study to Identify Branching Patterns," *The Journal of Hand Surgery*, Jan. 1991, vol. 16A, No. 1, p. 53-59.
Wattanapanitch, W. et al., "An Energy-Efficient Micropower Neural Recording Amplifier," *IEEE Transactions on Biomedical Circuits and Systems*, Jun. 2007, vol. 1. No. 2, p. 136-147.
Xu, J. et al., "A 160 µW 8-Channel Active Electrode System for EEG Monitoring," *IEEE Transactions on Biomedical Circuits and Systems*, Dec. 2011, vol. 5, No. 6, p. 555-567.
Yazicioglu, R. et al., "A 60 µW 60 nV/Hz Readout Front-End for Portable Biopotential Acquisition Systems," *IEEE Journal of Solid-State Circuits*, May 2007 vol. 42, No. 5, p. 1100-1110.
Yin, M. et al., "A Low-Noise Preamplifier with Adjustable Gain and Bandwidth for Biopotential Recording Applications," *IEEE International Symposium on Circuits and Systems*, May 2007, ISCAS 2007, p. 321-324.
Yoshida, K. et al., "Closed-Loop Control of Ankle Position Using Muscle Afferent Feedback with Functional Neuromuscular Stimulation," *IEEE Transactions on Biomedical Engineering*, Feb. 1996, vol. 43, No. 2, p. 167-176.
Yoshida, K. et al., "Characterization of Signals and Noise Rejection with Bipolar Longitudinal Intrafascicular Electrodes," *IEEE Transactions on Biomedical Engineering*, Feb. 1999, vol. 46, No. 2, p. 226-234.
Zhang, F. et al., "Design of Ultra-Low Power Biopotential Amplifiers for Biosignal Acquisition Applications," *IEEE Transactions on Biomedical Circuits and Systems*, Aug. 2012, vol. 6, No. 4, p. 344-355.
Zheng, X. et al., "Longitudinally Implanted Intrafascicular Electrodes for Stimulating and Recording Fascicular Physioelectrical Signals in the Sciatic Nerve of Rabbits," *Microsurgery*, 2003, vol. 23, No. 3, p. 268-273.
Zumsteg, Z. et al., "Power Feasibility of Implantable Digital Spike Sorting Circuits for Neural Prosthetic Systems," *IEEE Transactions on Neural Systems and Rehabilitation Engineering*, Sep. 2005, vol. 13, No. 3, p. 272-279.

\* cited by examiner

LOW NOISE ANALOG ELECTRONIC CIRCUIT DESIGN FOR RECORDING PERIPHERAL NERVE ACTIVITY

This invention was made with government support under a grant awarded from the National Institute of Health (NIH) under grant number NIH-R01EB008578. The government has certain rights in this invention.

BACKGROUND OF INVENTION

Though there have been many advances in prosthetic technology, existing systems are significantly limited in their ability to fully restore function after limb loss. Such limitations are manifested in the types of activities that can be achieved, the ease with which the tasks can be performed, and the richness of the experience. Improvements in state-of-the-art prosthetic technology can be achieved through fundamental advances in mechatronic systems, actuators, sensors, and control algorithms. However, truly advanced prosthetic systems require seamless integration of the intact sensory-motor living system with advanced, highly-capable artificial limbs, making it necessary to record neural activity to capture the motor-intent of the amputee.

It has been shown that despite partial atrophy and degeneration, both central and peripheral motor and somatosensory pathways retain significant function for many years following amputation—potentially allowing the use of neuroprosthetic technologies to establish efferent neural control of a prosthetic limb with direct afferent neural sensory feedback (Dhillon, Lawrence et al. 2004; Dhillon and Horch 2005; Dhillon, Kruger et al. 2005). Multiple electrode technologies currently exist to establish a neural interface. Choice of the electrode depends on many factors, including biocompatibility, long-term stability, ease of implantation, mechanical characteristics, electrochemical characteristics, and economics. Stimulation and recording can both be performed by electrodes placed either on the surface (surface electrodes) or beneath the skin (subcutaneous electrodes). Furthermore, subcutaneous electrodes can be placed on or in the muscle (epimysial or intramuscular electrodes), and on, in, or adjacent to peripheral nerves (extraneural or intraneural electrodes) (Keith 2001; Venkatasubramanian, Jung et al. 2006).

The current, most advanced hand and/or upper limb prostheses offer limited volitional motor control (Ohnishi, Weir et al., 2007). The primary pathway for the transmission of motor control information between the brain and muscle is through the peripheral nerves. Across numerous technologies, volitional motor control can be provided to a user at any level of the motor control pathway, but all of them require the recording of physiological signals. One approach is to record activity from peripheral nerves in the residual limb using longitudinal intrafascicular electrodes (LIFEs) and decode the signals to infer motor intent for the control of prostheses (Dhillon, Lawrence et al., 2004).

The few studies in which extracellular neural recordings from motor fascicles have been done in amputees using LIFEs indicate that the intrafascicular signal in the severed nerves has an ultra-low amplitude and broad shape. For example, when an amputee is attempting to generate activity of the missing limb, temporal 20 µV peak-to-peak signals can be obtained using intrafascicular recording (Dhillon, Lawrence et al., 2004). The signal-to-noise ratio is low, even with use of commercial recording systems (Dhillon, Lawrence et al., 2004; Lefurge, Goodall et al., 1991). Integrated circuits can be used for recording peripheral nerve activity (Uranga et al. 2004; Limunson et al. 2009; Rieger 2011). Often these use external components and are not always power/area efficient (200 µW/channel—order power and area above 0.06 mm$^2$ per channel). FIG. 7 presents a typical recording circuit where the first active circuit is an amplifier.

BRIEF SUMMARY

Embodiments of the subject invention provide implantable circuits and circuit systems to record activity (e.g., peripheral nerve activity). The circuits of the subject invention advantageously have good noise characteristics (e.g., low noise). Such circuits can have low power consumption and/or low area. In an embodiment, such an implantable circuit can be powered wirelessly.

Embodiments of the subject invention also provide methods of designing, manufacturing, and using an analog amplifier with low noise and low area consumption.

Embodiments of the subject invention also provide electronic circuits (e.g., implantable electronic circuits) and circuit systems for recording low amplitude neural signals. These circuits are fully implantable. In an embodiment, an electronic circuit records low amplitude neural signals and also rejects signals with frequency components outside a tunable bandwidth. In a further embodiment, an electronic circuit records low amplitude neural signals, rejects signals with frequency components outside a tunable bandwidth, and maintains a low area consumption.

Embodiments of the subject invention also provide electronic circuits (e.g., implantable electronic circuits) and circuit systems that allow processing of neural activity to extract features while maintaining good noise characteristics (e.g., low noise), with relatively low power consumption and low area consumption.

In one embodiment, a circuit includes a low noise amplifier, wherein the low noise amplifier comprises an operational transconductance amplifier (OTA) having at least two differential input series-connected transistors (SCT). The circuit can be fully implantable (e.g., in a human subject). The low noise amplifier can be configured such that: the area per channel of the low noise amplifier is no more than 0.05 mm$^2$; the power consumption per channel of the low noise amplifier is no more than 150 µW; and the input-referred noise density of the low noise amplifier is no more than 50 nV/(Hz$^{1/2}$) on 100 Hz-4 kHz bandwidth and no more than 30 nV/(Hz$^{1/2}$) on the main white Gaussian noise contribution over the full bandwidth. In a further embodiment, the power consumption per channel of the low noise amplifier is no more than 20 µW.

In another embodiment, a system for recording peripheral nerve activity includes: a circuit; and at least one electrode in operable communication with the circuit. The circuit includes a low noise amplifier, wherein the low noise amplifier comprises an OTA having at least two differential input SCTs. The circuit can be fully implantable (e.g., in a human subject), and the low noise amplifier can be configured such that: the area per channel of the low noise amplifier is no more than 0.05 mm$^2$; the power consumption per channel of the low noise amplifier is no more than 150 µW; and the input-referred noise density of the low noise amplifier is no more than 50 nV/(Hz$^{1/2}$) on 100 Hz-4 kHz bandwidth and no more than 30 nV/(Hz$^{1/2}$) on the main white Gaussian noise contribution over the full bandwidth. In a further embodiment, the power consumption per channel of the low noise amplifier is no more than 20 µW.

In yet another embodiment, a method of recording peripheral nerve activity includes: implanting at least one electrode in or on at least one peripheral nerve; providing a circuit in operable communication with the at least one electrode; and recording activity of the at least one peripheral nerve using the circuit. The circuit includes a low noise amplifier, wherein the low noise amplifier comprises an OTA having at least two differential input SCTs. The circuit can be implantable (e.g., in a human subject), and the low noise amplifier can be configured such that: the area per channel of the low noise amplifier is no more than 0.05 mm$^2$; the power consumption per channel of the low noise amplifier is no more than 150 µW; and the input-referred noise density of the low noise amplifier is no more than 50 nV/(Hz$^{1/2}$) on 100 Hz-4 kHz bandwidth and no more than 30 nV/(Hz$^{1/2}$) on the main white Gaussian noise contribution over the full bandwidth. In a further embodiment, the power consumption per channel of the low noise amplifier is no more than 20 µW.

In yet another embodiment, an electronic circuit is configured to process neural activity to extract features. The circuit is configured such that: the area per channel of the circuit is no more than 0.05 mm$^2$; the power consumption per channel of the circuit is no more than 150 µW; and the input-referred noise density of the circuit is no more than 50 nV/(Hz$^{1/2}$) on 100 Hz-4 kHz bandwidth and no more than 30 nV/(Hz$^{1/2}$) on the main white Gaussian noise contribution over the full bandwidth. In a further embodiment, the power consumption per channel of the circuit is no more than 20 µW.

DETAILED DISCLOSURE

Embodiments of the subject invention provide implantable circuits and circuit systems to record activity (e.g., peripheral nerve activity). The circuits of the subject invention advantageously have good noise characteristics (e.g., low noise). Such circuits can have low power consumption and/or low area. In an embodiment, such an implantable circuit can be powered wirelessly.

Embodiments of the subject invention also provide methods of designing, manufacturing, and using an analog amplifier with low noise and low area consumption.

Embodiments of the subject invention also provide electronic circuits (e.g., implantable electronic circuits) and circuit systems for recording low amplitude neural signals. In an embodiment, an electronic circuit records low amplitude neural signals and also rejects signals with frequency components outside a tunable bandwidth. In a further embodiment, an electronic circuit records low amplitude neural signals, rejects signals with frequency components outside a tunable bandwidth, and maintains a low area consumption.

Embodiments of the subject invention also provide electronic circuits (e.g., implantable electronic circuits) and circuit systems that allow processing of neural activity to extract features while maintaining good noise characteristics (e.g., low noise), with relatively low power consumption and low area consumption.

Implantable circuits and circuit systems of the subject invention can be used to record activity from peripheral nerves in order to decode motor intent for seamless volitional control of prostheses. Such circuitry can be particularly applicable to recording intrafascicular signals from upper or lower extremities of amputees. Circuitry of the subject invention can be used for many purposes, including recording any peripheral nerve activity or brain activity.

In many embodiments, an analog circuit system is capable of recording activity from peripheral nerves and is implemented in a standalone integrated circuit (IC). The system includes the following cascaded analog sub-circuits: a low noise amplifier; a highpass filter with tunable corner frequency; and a programmable discrete gain amplifier. The output of this system can be accessible either directly or after processing through additional circuitry to provide information about the neural activity feature. Such a system advantageously associates two techniques, which may be used separately for different applications, for the design of the low noise amplifier. The system is a low power, low noise, low area amplifier.

Figure 1:
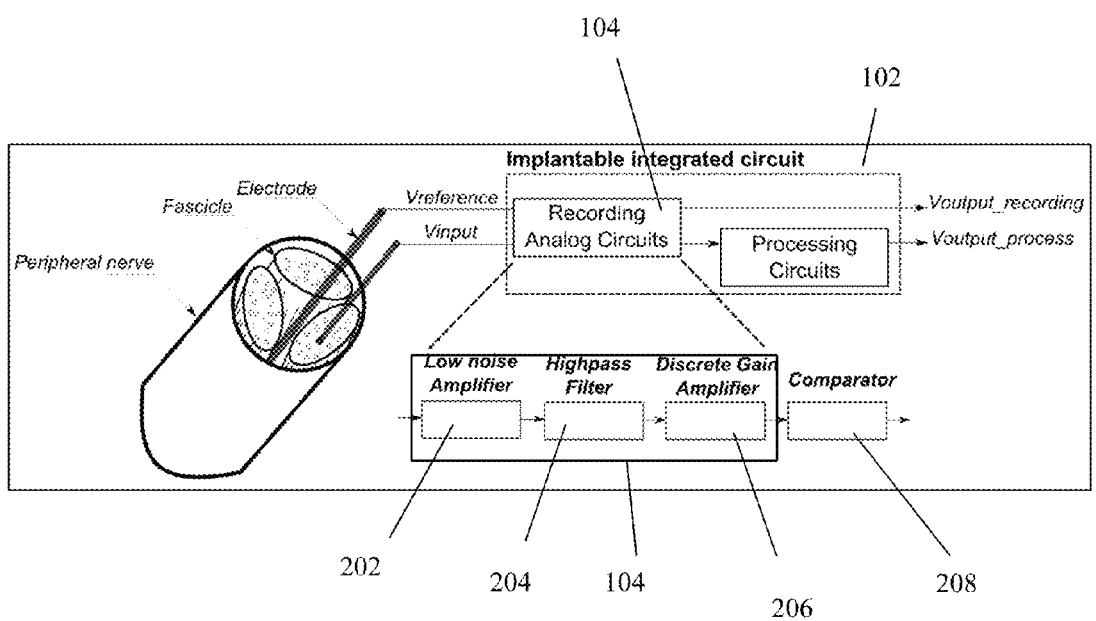
FIG. 1 shows a schematic of an analog circuit system according to an embodiment of the subject invention.

FIG. 1 shows a schematic of an analog circuit system according to an embodiment of the subject invention. The circuit system can record activity (e.g., using an internal or external electrode) from peripheral nerves and can be implemented in a standalone integrated circuit. Electrodes that can be used with systems of the subject invention are discussed in more detail below. The system can include an implantable IC 102 including recording analog circuits 104 and, optionally, one or more processing circuits. The recording analog circuits 104 can include one or more of a low noise amplifier 202, a highpass filter 204, and a discrete gain amplifier 206. The low noise amplifier 202 can be a first stage of the recording analog circuits 104, highpass filter 204 can be a second stage, and the discrete gain amplifier 206 can be a third stage. The highpass filter 204 can have a tunable corner frequency, and the discrete gain amplifier 206 can be programmable. The output of the system can be accessed either directly or after additional processing circuitry that yields specific information about features of the recorded neural activity (e.g., spiking rate). In a particular embodiment, the processing circuits can include a comparator 208. The recording analog circuits 104 utilize an advantageous method for designing the first stage amplifier to achieve low noise, low power, and low area.

A circuit or circuit system can have an area per channel of, for example, any of the following values, about any of the following values, no more than any of the following values, or less than any of the following values (all numerical values are in square millimeters): 1, 0.9, 0.8, 0.7, 0.6, 0.5, 0.4, 0.3, 0.2, 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001. This can be the area per channel of the low noise amplifier 202, the area of the recording analog circuits 104, or the area of the recording analog circuits 104 together with any processing circuits (102). For example, the area per channel can be no more than 0.1 mm$^2$ or 0.05 mm$^2$. In a particular embodiment, the area per channel is in a range of from 0.0001 mm$^2$ (100 μm$^2$) to 0.05 mm$^2$.

A circuit or circuit system can have a power consumption (e.g., a power consumption per channel) of, for example, any of the following values, about any of the following values, no more than any of the following values, or less than any of the following values (all numerical values are in micro-Watts): 500, 400, 300, 200, 197, 150, 100, 50, 45, 40, 35, 34, 33, 32.5, 32, 31, 30, 25, 20, 15, 10, 9, 8, 7, 6, 5, 4, 3, 2, 1, 0.9, 0.8, 0.7, 0.6, 0.5, 0.4, 0.3, 0.2, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001. This can be the power consumption of the low noise amplifier 202, the power consumption of the recording analog circuits 104, or the power consumption of the recording analog circuits 104 together with any processing circuits (102). This can also be power consumption per channel or of the whole circuit. For example, the power consumption per channel can be no more than 150 μW or no more than 20 μW. In a particular embodiment, the power consumption per channel is in a range of from 0.005 μW (5 nW) to 20 μW.

A circuit or circuit system can have an input-referred voltage noise density of, for example, any of the following values, about any of the following values, no more than any of the following values, or less than any of the following values (all numerical values are in nano-Volts per square root of Hertz (nV/(Hz$^{1/2}$))): 100, 90, 80, 70, 60, 50, 40, 30, 25, 24, 23, 22.8, 22, 21, 20, 19, 18, 17.7, 17, 16, 15, 14, 13, 12, 11, 10, 9, 8, 7, 6, 5, 4, 3, 2, or 1. This can be, e.g., the input-referred voltage noise density of the low noise amplifier 202. These values can refer to the input-referred voltage noise density over a bandwidth (e.g., 100 Hz-4 kHz) or to the main white Gaussian noise contribution over the full bandwidth. For example, the input-referred noise density of the circuit can be no more than 50 nV/(Hz$^{1/2}$) on 100 Hz-4 kHz bandwidth and no more than 30 nV/(Hz$^{1/2}$) on the main white Gaussian noise contribution over the full bandwidth.

Circuits and circuit systems according to embodiments of the subject invention provide the capability of recording neural signals from peripheral nerves that often have low amplitude (e.g., approximately 15 μV to 60 μV peak-to-peak or less than 60 μV peak-to-peak) on a bandwidth spanning hundreds of Hertz to a few kilo-Hertz (typically from 100-500 Hz to 5-10 kHz, or any range therebetween). Requirements for peripheral nerve recording are discussed in more detail below. Analog recording circuits of the subject invention can be provided on a chip designed to be fully implanted into a subject (e.g., a human subject such as an amputee).

The design of the first stage low noise amplifier combines a shared operational transconductance amplifier (OTA) recording system architecture with differential input series-connected transistors (SCT) (e.g., two such differential input SCTs). The OTA architecture can be that as described in Majidzadeh, Schmid et al., 2011. It is designed to reduce power and size consumption. FIG. 2a shows a schematic of a shared OTA architecture with a conventional structure of an array of n neural amplifiers (Majidzadeh, Schmid et al., 2011). FIG. 2b shows a partial OTA sharing structure for an array of n neural amplifiers, where the shaded box identifies the circuit shared among all low noise amplifiers.

Figure 3:
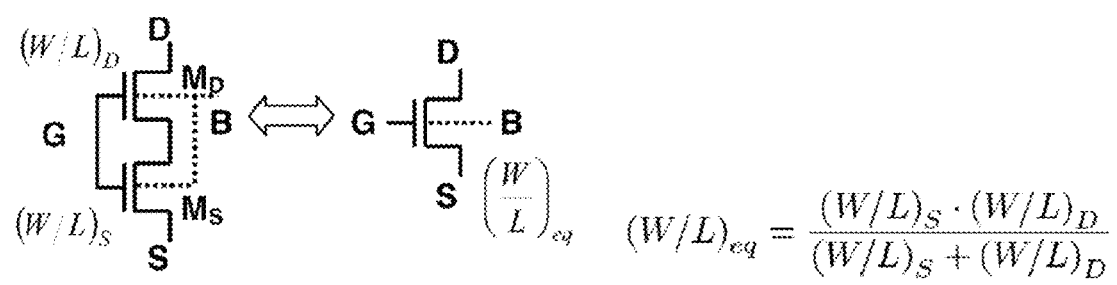
FIG. 3 shows a schematic of two series connected transistors (SCTs).

In many embodiments, the shared OTA architecture is altered by adding SCT circuitry to permit further reduction of the noise and area consumption. An SCT has been used for a different purpose previously—to achieve low transconductance in integrated low frequency filters (Arnaud, Fiorelli et al. 2006). FIG. 3 shows an SCT that can be used as part of a circuit according to many embodiments of the subject invention. The additional SCT circuitry decreases the Cgd parasitic capacitance, as a function of the transistor width (Razavi 2003). A new parameter F helps to decrease the noise and area consumption, and increase the gain performance. The new parameter F is the width ratio of the differential input SCT, defined as follows:

$$F = \frac{W(Mia)}{W(Mib)},$$

where W(M) is the width W of the transistor M, and Mia and Mib are the differential input SCT of each branch of the OTA.

Figure 4:
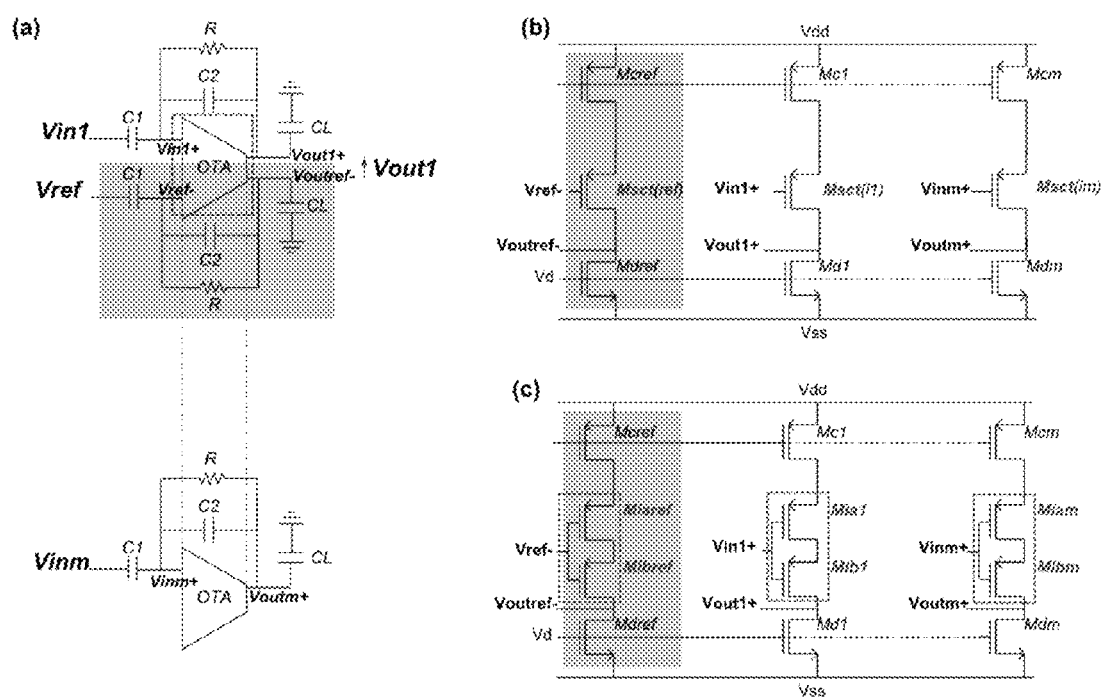
FIG. 4a shows a schematic of a circuit according to an embodiment of the subject invention, including a low noise amplifier.
FIG. 4b shows a schematic of a shared OTA recording system architecture according to an embodiment of the subject invention.
FIG. 4c shows a schematic of a shared OTA-SCT according to an embodiment of the subject invention.

FIG. 4 shows a shared SCT-OTA recording system architecture according to an embodiment of the subject invention. The use of the SCT circuit along with the shared OTA architecture advantageously and surprisingly results in a low power, low noise, low area amplifier. Shaded boxes in FIG. 4 identify the shared circuit among all low noise amplifiers. FIG. 4a shows the full amputee peripheral nerve recording, including the low noise amplifiers. One low noise amplifier is required for each recording circuit (one per recording electrode). The dashed box identifies the enhanced OTA with SCT. FIG. 4b shows a schematic of a shared OTA recording system architecture according to an embodiment of the subject invention. Msct transistors are the SCTs. FIG. 4c shows a detailed schematic of a shared OTA-SCT according to an embodiment of the subject invention. Referring to FIG. 4c, instead of using one single transistor on the OTA differential pair, two SCTs are used—$M_{ia}$, and $M_{ib}$, sized with $(W_1/L_1)_{Mia}$ and $(F \cdot W_1/L_1)_{Mib}$, where $W_1$ and $L_1$ are the common width and length parameters of the input transistors, and F is a multiplicative factor for area/noise efficient sizing. F is a new parameter that allows tuning of the characteristics of the amplifier. This new design paradigm advantageously and surprisingly results in a low power, low noise, low area amplifier.

In an embodiment, an implantable circuit includes an OTA enhanced with at least two SCTs. The SCT-OTA can be in operable communication with at least one electrode.

In an embodiment, a circuit system can include an SCT-OTA as described herein, a highpass filter as described herein in operable communication with the SCT-OTA, and a discrete gain amplifier in operable communication with the highpass filter. In a further embodiment, the circuit system includes at least one electrode in operable communication with the SCT-OTA. In yet a further embodiment, the circuit system includes at least one processing circuit in operable communication with the discrete gain amplifier. The at least one processing circuit can be, for example, a comparator (e.g., a Schmitt trigger), though embodiments are not limited thereto. The SCT-OTA can be a first stage of the circuit system, the highpass filter can be a second stage of the circuit system, and the discrete gain amplifier can be a third stage of the circuit system.

As used herein, and unless otherwise specifically stated, the terms "operable communication" and "operably connected" mean that the particular elements are connected in such a way that they cooperate to achieve their intended function or functions. The "connection" may be direct or indirect, physical (e.g., by wires or other physical connections) or remote (e.g., wireless).

In an embodiment, the highpass filter can be a filter such as a passive resistor-capacitor filter circuit. This filter provides the ability to tune the bandwidth. For example, the filter can be capable of tuning the bandwidth in a range of about 100 Hz and 500 Hz. The filter does not degrade the gain characteristics provided by the low noise amplifier (first stage). Hence, the input impedances must be properly tuned.

The discrete gain amplifier (e.g., third stage programmable discrete gain amplifier) can further amplify the signal so that it can be efficiently utilized. The discrete gain amplifier can provide the capability for adapting the output of the second stage high pass filter to the dynamic input voltage/current range of the additional processing circuitry (if present).

In an embodiment, additional processing circuitry can be provided. Such processing circuitry can, for example, provide control signals to control the motors of a prosthesis. In a particular embodiment, additional processing circuitry can include a comparator, such as a Schmitt trigger.

Figure 6:
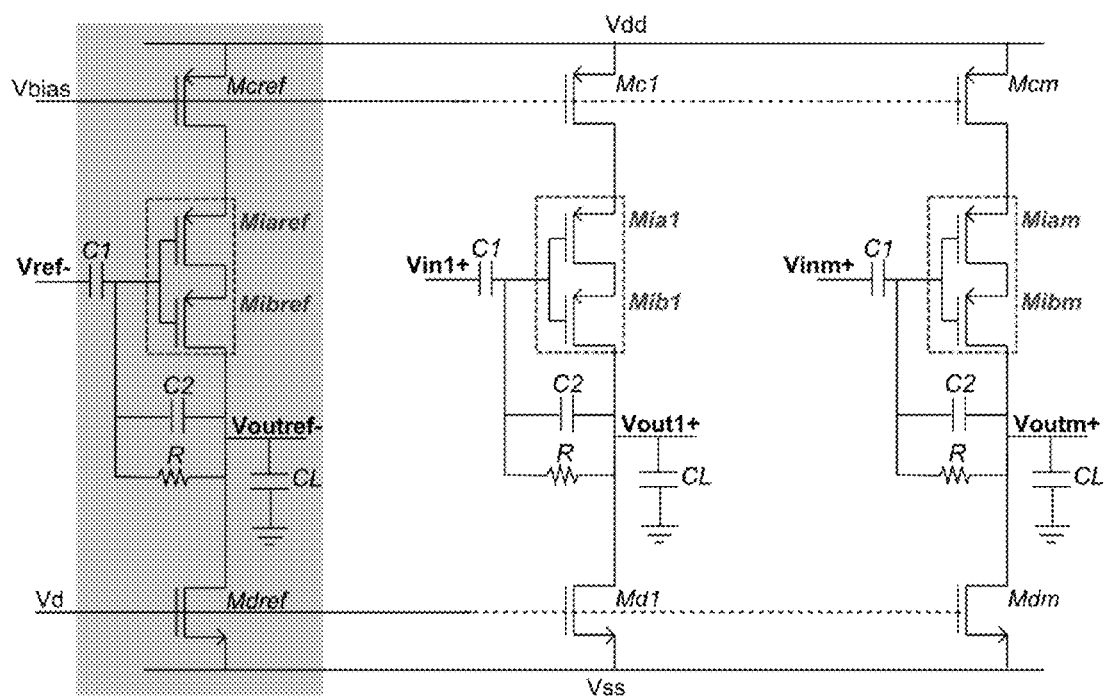
FIG. 6 shows a schematic of a circuit according to an embodiment of the subject invention.

FIG. 6 shows a schematic of a circuit according to an embodiment of the subject invention. Referring to FIG. 6, the shared low noise amplifier suitable for peripheral nerve recording includes m amplifiers represented on the schematic. One low noise amplifier is required for each recording circuit (one per recording electrode), which includes: the reference shared negative branch (shaded area); and a positive input branch (Vin p+, pεm). The two branches define the OTA for each low noise amplifier. The shaded box identifies the shared branch circuit among all low noise amplifiers. The dashed box identifies the two SCTs as the input transistor of one branch of the OTA. Instead of using one single transistor on the OTA differential pair, two SCTs ($M_{ia}$ and $M_{ib}$) are used, sized with $(W_1/L_1)_{Mia}$ and $(F. W_1/L_1)_{Mib}$, where $W_1$ and $L_1$ are the common width and length parameters of the input transistors, and F a multiplicative factor for area/noise efficient sizing. F is a new parameter that allows tuning of the characteristics of the amplifier.

In an embodiment, a method of recording peripheral nerve activity includes using an implantable circuit or circuit system as described herein to record the nerve activity. Circuits and circuit systems as described herein can also be used with any neural recording system that requires amplification of low amplitude signals with low noise and broad bandwidth.

Embodiments of the subject invention also provide methods of fabricating circuits or circuit systems as described herein.

The input-referred voltage noise density of a low noise amplifier according to embodiments of the subject invention can be characterized by the main noise contribution over a bandwidth (e.g., from a minimum frequency, f_min, to a maximum frequency, f_max). The main noise contribution at low frequency is the Flicker noise (1/f noise) and at high frequency is the white Gaussian noise. The subject invention minimizes the Flicker noise and in general the noise contribution in the low frequencies due to the architecture.

Figure 7:
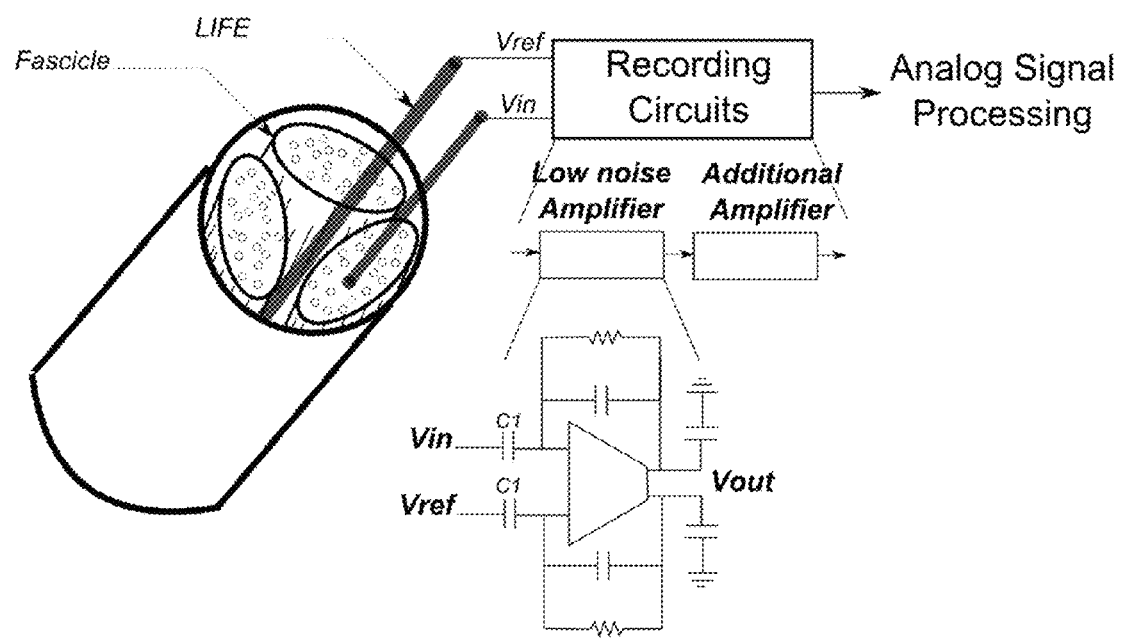
FIG. 7 shows a schematic of a conventional recording circuit.

In conventional amplifies, the Flicker noise is not considered and only white noise of the components of the low noise amplifier architecture is considered (Harrison and Charles 2003, e.g., FIG. 7). If the Flicker noise is also considered, as in the subject invention, then the noise contribution on low frequencies can be very important and not negligible. Hence, the corner frequency is the characteristic frequency to describe at which frequency the low frequency noise switches, from being the main contributor to the overall noise of the low noise amplifier, to being a secondary contributor.

Circuits and circuit systems of the subject Mention meet the required noise performance, power consumption, and area consumption of an integrated circuit required for recording from multiple electrodes. Circuits and circuit systems of the subject Mention can be used with any number of electrodes implanted in peripheral nerves. While existing integrated circuits have power and size consumptions that forbid any future high density integration, embodiments of the subject invention overcome these disadvantages.

Low noise amplifiers of the subject invention can use a single additional parameter (F) to design the circuit for low noise and low area consumption, thereby providing a new design paradigm. A set of small transistors can be used in place of a single large transistor in part of the circuit. It is not expected that a combination of smaller transistors will yield the same noise performance as a bigger transistor, but they surprisingly did. This use of smaller transistors provides the benefit of reduced size to the overall architecture. Thus, the overall amplifier has both low noise and low area consumption. The low power consumption derives, at least in part, from the shared architecture.

Embodiments of the subject invention achieve good gain characteristics for the low noise amplifier while also achieving good noise performance (i.e., low noise). The parastic capacitance of the input OTA component of the low noise amplifier circuit can be modified. A two-SCT architecture can be used for the design of the parasitic capacitance to decrease the parasitic capacitance. A single additional parameter (F) can be utilized to achieve this reduced capacitance and provide a new design paradigm. It was not expected that a combination of smaller transistors would yield the same noise performance as a bigger transistor, but such noise performance was achieved. This use of smaller transistors provides the benefit of reduced size to the overall architecture. Thus, the overall amplifier has both low noise and low area consumption.

Electrodes

Extraneural electrodes are often of the "cuff" type. Examples are: (Stein, Charles et al. 1975; Naples, Mortimer et al. 1988; Figoni, Glaser et al. 1991; Sweeney, Crawford et al. 1995; Grill 2000; Navarro, Valderrama et al. 2001; Jensen, Sinkjaer et al. 2002). Cuff dimensions, mechanical properties and materials, and the configuration of the active and indifferent sites are important. The main limitation of "cuff electrodes", however, is that their sensitivity level for both stimulation and recording lies at the level of the whole nerve. This can be problematic, as each peripheral nerve is made up of many heterogeneous motor and sensory axons, and true integration of neuroprosthetics will likely require sensitivity at the fascicular or axonal level (Zheng, Zhang et al. 2003). To access the fascicles, an intraneural electrode approach is required. Three main types of intraneural electrodes exist: regeneration electrodes (or sieve chips), multielectrode arrays, and single needle (Yoshida and Riso 2004).

Regeneration electrodes (or sieve chips) have been in development for nearly two decades with limited success (Edell 1986; Kovacs, Storment et al., 1992). Even in what may be the best result to date (in a fish vestibular nerve; (Mensinger, Anderson et al. 2000) only a limited number of channels with nerve fibers growing through them were able to produce definitive recordings. The most probable issues lie in the distance of the recording site to a node or blockage of nerve conduction as fibers pass through the small holes in the array. Modifications to the pore size and thickness of the chips may produce better results; however, extensive proof of principle studies would be required before these electrodes could be integrated into a prosthesis.

Anatomical and physiological constraints dictate that an effective peripheral nerve interface for providing discrete, distally referred sensations and for obtaining movement specific command signals from peripheral nerve stumps, must place electrode sites within the perineurium of individual nerve fascicles. This could be accomplished using punctate penetrating arrays such as the Utah multielectrode array (Branner and Normann 2000) or the slowly penetrating electrode (Malmstrom, McNaughton et al. 1998) or individual intrafascicular electrodes such as the longitudinal intrafascicular electrodes (LIFEs) developed in the Horch lab (Malagodi, Horch et al. 1989).

The Utah electrode array, originally designed to record and stimulate cortical tissue, with 100 electrodes in a 10×10 array measures as small as 2 mm$^2$ with each 1 mm-long electrode spaced 400 µm apart (Campbell, Jones et al. 1991). It has been implanted in cat sciatic nerves chronically (Branner and Normann 2000; Branner, Stein et al. 2004). The development of the high density multi-micro electrode arrays, such as Utah Electrode Arrays, allows access to a larger population of fibers in the nerve and could allow recording from multiple electrodes of an array (Branner and Normann 2000; McDonnall, Clark et al. 2004). The lead wires for multiple electrodes can produce tethering forces on the array, resulting in damage to the nerve (Branner, Stein et al. 2004). Their implantation procedure also does not allow for the specific alignment of electrodes with specific fascicles. In addition, the implanted array has to be securely fixed to the nerve. These multiple challenges remain to be addressed for practical application in human subjects currently.

Another approach is to use LIFEs. These electrodes are a proven technology that has been shown to provide largely stable recordings and localized stimulation in chronic animal studies, and is the only technology proven to do the same in human amputee nerve stumps on a semi-chronic basis (Goodall, Lefurge et al. 1991; Lefurge, Goodall et al. 1991; Dhillon and Horch 2005; Dhillon, Kruger et al. 2005; Rossini, Rigosa et al. 2011). These electrodes allow access to individual fascicles and recording site exposure of 1 mm or more thereby providing improved recording capability (Malagodi, Horch et al. 1989). The somatotopic organization of peripheral nerves at both the fascicular and sub-fascicular levels (Hallin 1990; Watchmaker, Gumucio et al. 1991; Hallin and Wu 2001) allows directed access using LIFEs and is an asset for the circuits and circuit systems of the subject invention. Thus, in an embodiment of the subject invention, a circuit or circuit system as discussed herein is configured to interface with one or more LIFEs. In a further embodiment, a circuit or circuit system as discussed herein includes one or more LIFEs.

Peripheral Nerve Recording Requirements

FIG. 4a shows a recording system for peripheral nerve application. The intrafascicular activity, i.e., the signal-of-interest, has an ultra-low amplitude (in the range of microvolts). One of the primary aims of the recording system, if not the primary aim, is to amplify this ultra-low amplitude signal to be efficiently processed by the following signal processing circuits.

Every electronic circuit has an intrinsic noise. This parasitic noise signal should not have a higher amplitude than the signal-of-interest. As illustrated by the Friis formula (Ziel 1970), the overall recording system noise is primarily established by the noise of the first amplifier, called the low noise amplifier. Hence, the noise of the low noise amplifier should be as low as possible. To provide an efficient amplification, the following requirements need to be quantitatively defined: the signal-of-interest amplitude, the recording system amplification gain, and the noise specification of the low noise amplifier.

Electronic noise can be diminished by increasing the transistor area and/or increasing the power consumption. At the transistor level, such a feature is sometime represented by the transconductance-to-current ratio ($G_m/I_D$), where the transconductance is proportional to the transistor size (Razavi 2003). Therefore, a challenge for integrated recording systems is to find the best trade-off between the noise performance and the area/power consumption.

According to amputee peripheral nerve recording, implanted electrode in nerves on every level (cuff-recording, intra-nerve recording, intrafascicular recording with LIFE) record both nerve activity and nearby muscle activity (electromyograms, or EMG). In recording nerve activity, the only signal-of-interest is the intrafascicular activity; the EMG signal is then labeled as a parasitic signal. A second aim of the recording system is to reject parasitic signals, such as an EMG signal, from nearby muscles or other external parasitic sources.

The EMG signal should be characterized in order to select the appropriate parasitic rejection method. On one hand, the EMG spectrum is defined from 1 Hz to 3 kHz with a peak at about 250 Hz (Nikolic, Popovic et al. 1994). On the other hand, the amputee intrafascicular activity is described as a broad-shape spike (unlike the sharp-shape spike from microelectrode brain recording). The intrafascicular spike can be as broad as 4 to 6 milliseconds (the fundamental frequency would be about 150 to 250 Hz, with additional harmonic frequencies). Therefore, the EMG spectrum is large enough to overlap with the intrafascicular spectrum. Such overlap could lead to false intrafascicular activity signal processing. Because the intrafascicular and EMG signals share the same spectrum, their amplitude characteristics should be defined. Based on a cuff-recording study, EMG amplitude was described to be several orders of magnitude larger than nerve activity (Nikolic, Popovic et al. 1994). As for intrafascicular recording, the perineurium could potentially be insulated (Yoshida and Stein 1999).

To provide an efficient parasitic rejection, several methods can be used: shielding, differential recording; filtering; and common-mode rejection. Therefore, the additional following requirements need to be quantitatively defined: filtering bandwidth; and the recording system amplification common-mode rejection gain. To characterize the parasitic rejection in electronics, the common-mode gain rejection ratio (CMRR) is typically used. The CMRR is defined as the ratio between the differential and common mode gains.

The signal-of-interest is the intrafascicular activity by LIFEs differential recording. It has been shown that when an amputee attempts to generate activity of the missing limb, temporal 20 µV peak-to-peak (pp) signals can be obtained using intrafascicular recordings (Dhillon, Lawrence et al. 2004). Intrafascicular nerve recordings in animal models have been elicited by tactile or electrical stimulation delivered to the limb or nerve. The elicited activity peak-to-peak amplitude ranges between 10 to 20 $\mu V_{pp}$ (Goodall, Lefurge et al. 1991; McNaughton and Horch 1994) and 40 to 60 $\mu V_{pp}$ (Malagodi, Horch et al. 1989), respectively, for cat's radial and rat's sciatic nerve. On one hand, it has been reported that spontaneous sensory activity has larger average amplitude than evoked single units (Yoshida and Stein 1999). On the other hand, recorded activity could represent single action potentials or overlapped action potentials that derive from multiple neurons within a motor pool, which could explain the broad shape and low amplitude of the intrafascicular signal recorded from amputees.

In an embodiment of the subject invention, the range of recordable activity can be from about 10 $\mu V_{pp}$ to about 60 $\mu V_{pp}$.

The recording system primary aim is to amplify the signal-of-interest. The overall gain for peripheral nerve recording is consistent in the literature, in the order of 10 kV/V (Malagodi, Horch et al. 1989; Yoshida and Horch 1996; Dhillon, Lawrence et al. 2004). With such amplification, the output of the recorded signal is expected to be in the hundreds of millivolt range for a 10 $\mu V_{pp}$ input amplitude. Integrated recording systems could target a lower amplitude for the recording signal to be processed on chip using low voltage bias. Published nerve recording systems offered an overall gain in the range of 1-5 kV/V (Uranga, Navarro et al. 2004; Limnuson, Tyler et al. 2009).

In an embodiment of the subject invention, the gain of the low noise amplifier is from 5 kV/V to 30 kV/V. In a preferred embodiment, the gain is at least 10 kV/V or at least about 10 kV/V. In a particular embodiment, the gain is 10 kV/V or about 10 kV/V. Since differential recording is applied to improve the parasitic rejection, the overall gain can also be defined as the differential gain. The device noise contribution should be low enough to allow the detection of intrafascicular activity. The noise specification is characterized by two performances.

The first noise specification is quantified by the input referred noise of the recording system, especially the low noise amplifier. The input referred noise could be represented by a noise density or a root mean square (RMS) value. The input referred noise density allows noise performance comparison between amplifiers with different gain and filter bandwidth. Indeed, electronic amplifiers don't have a constant gain over the full spectrum; because of parasitic electronic components, the amplifier may be better represented by a bandpass filter. The RMS noise is an average noise value over a defined bandwidth of integration, which includes the signal-of-interest spectrum.

The second noise specification is quantified by the signal-to-noise ratio (SNR). The SNR specification includes the input referred noise specification. The SNR is defined in the literature by different amplitude units, such as peak-to-peak, root-mean-square or standard deviation, with or without nulling the DC signal average (Kyung Hwan and Sung June 2000; Obeid 2007; Nabar and Rajgopal 2009). For the sake of clarity, SNR unit and/or definition is provided for each review.

The input referred noise of the recording system can be quantified by taking into account several features: the intrinsic noise of LIFE; the SNR of the intrafascicular activity measured by a commercial recording system; and the typical SNR to ease future signal processing (e.g. threshold detection).

In many cases, a LIFE is metal. Because the LIFE is metal, it has intrinsic thermal noise. For power/area reduction, there may not be a need to design a low noise amplifier with a lower noise than the LIFE-intrinsic thermal noise. Therefore, the LIFE-intrinsic thermal noise can define the minimal noise of the low noise amplifier. The LIFE equivalent impedance at 1 kHz range is between 8 and 12 k$\Omega$ according to the maxima of the standard deviation of LIFE impedance measurement from 2- to 6-month implantation in cats (Lefurge, Goodall et al. 1991). The LIFE-intrinsic thermal noise is expected to be in a range of 0.7-0.9 $\mu$Vrms over 4 kHz. The noise bandwidth of integration is chosen to include the activity spectrum while not being too large to be compared with most of published recording studies (Malagodi, Horch et al. 1989; Yoshida and Horch 1996; Yoshida and Stein 1999; Dhillon, Lawrence et al. 2004). The LIFE-intrinsic RMS noise is equivalent to the usual thermal noise from cuff-electrodes, which is about 0.7$\mu$ $V_{RMS}$ (Stein, Nichols et al. 1977).

In sensory nerve recording studies using cuff-electrode or LIFE using bandpass filter amplification, SNRs measured with commercial instruments within 0-3 dB range have been reported (Malagodi, Horch et al. 1989; Lefurge, Goodall et al. 1991; Goodall and Horch 1992; Upshaw and Sinkjaer 1998). Such 0-3 dB SNR was qualified as a low SNR by authors. With regard to motor control activity, a recorded signal can be used with a Schmitt trigger-based process to control motion (Dhillon, Lawrence et al. 2004). The minimum threshold level for detecting neural activity was set manually, no SNR values are reported but it could be defined as approximately 3-6 dB according to the peak-to-peak maximal signal-to-noise ratio that was calculated from the presented data.

A qualitative SNR description is usually given to describe the ease of extracting information. The detection application of the studies is the brain spike detection. Even if brain spike has a different signal characteristic than amputee peripheral nerve signals, these comparative studies provide realistic quantification of SNR vs. detection efficiency, which can be used as a starting point applications of the subject invention. In a computational comparative study, a spike detector method can have performance scored as small (SNR≤1.8), medium (2.6≤SNR≤3.0), and large (SNR≥3.4) (Obeid and Wolf 2004). Other computational comparative spike sorting methods (which include a spike detection feature) use the following SNR ranges: 5-20 as the ratio of the mean peak signal level to the standard deviation of the background noise measured using segments of data that do not contain spikes (Zumsteg, Kemere et al. 2005); −10 dB-20 dB as the peak-to-peak amplitude of the average spike shape over six standard deviations of the noise (Gibson, Judy et al. 2010); and 1-2.5 as the average of the absolute peak amplitude of a spike over 3 RMS pure noise (Shalchyan, Jensen et al. 2012).

Based on the two previous reviews (SNR of the intrafascicular activity measured by a commercial recording system and the typical SNR to ease future signal processing), the maximum acceptable SNR can be defined, and therefore the maximal noise of the low noise amplifier can be defined for the minimal recordable signal-of-interest amplitude (e.g., 10 $\mu V_{pp}$). The SNR can be defined as the ratio of the intrafascicular signal peak-to-peak amplitude to two standard deviations of background noise. This definition is based on the expectation that the maximal peak-to-peak noise amplitude will be close to 6 standard deviations. Based on the statistical definition, there is a 66% chance that the maximum noise amplitude is three times the RMS noise average to peak amplitude voltage.

First, the maximal SNR needs to be defined. If the minimal amplitude (10 $\mu V_{pp}$) and the LIFE intrinsic noise (0.7 $\mu V_{RMS}$) are considered, then the best recording system SNR is 7.14 V/V (17 dB). This SNR represent the best SNR that could be recorded if the electronic system was noiseless.

The usual "high" SNR is defined as 5 or 6 dB, which leads to a resultant RMS noise of 0.8-1 $\mu V_{RMS}$. According to a published SNR vs. detection efficiency study (Obeid and Wolf 2004), an SNR higher than 3.4 would be enough for sharp-shape brain spike detection. This 3.4 dB SNR is close to the minimum acceptable SNR (3 dB) for intrafascicular recording studies. The resultant RMS noise would be 1.6 $\mu V_{RMS}$.

The input referred noise over 4 kHz can be defined as excellent if it is in the range of 0.7-1 $\mu V_{RMS}$, and acceptable if it is in the range of 1-1.6 $\mu V_{RMS}$. This definition is a rough estimation; extensive study takes into account the different noise nature impact (Flicker vs. thermal noise).

of-interest by an output attenuation factor (labeled N). The resultant CMRR is then defined as the ratio between the input parasitic signal amplitude by N and the input signal-of-interest. The CMRR is independent of the differential and common gains, which is represented by the N factor instead. Table 1 illustrates the different cases of couple input signal-of-interest/parasitic signal amplitude for N sets at 10 and 100. The CMRR range is 100V/V to 1 MV/V (40-120 dB).

In an embodiment, the CMRR can be defined to be between 30 kV/V and 1 MV/V (90 to 130 dB). Referring to Table 1, this can lead to a common-mode gain of 0.01-0.3 V/V (−40 dB to −10 dB) for a differential gain of 10 kV/V (80 dB).

TABLE 1

CMRR vs. output attenuation factor N

| Input signal-of-interest amplitude ($\mu V_{pp}$) | Input parasitic signal (EMG) amplitude ($mV_{pp}$) | Differential Gain Ad (kV/V) | Output signal-of-interest amplitude (mVpp) | output attenuation factor N (V/V) | Output parasitic signal (EMG) amplitude ($mV_{pp}$) | Common-mode Gain Ac (V/V) | Common-mode Gain Ac (dB) | CMRR = Ad/Ac (V/V) | CMRR (dB) |
|---|---|---|---|---|---|---|---|---|---|
| 10 | 0.1 | 10 | 100 | 10 | 10 | 100 | 40 | 100 | 40 |
|  | 1 |  |  |  |  | 10 | 20 | 1k | 60 |
|  | 10 |  |  |  |  | 1 | 0 | 10k | 80 |
|  | 100 |  |  |  |  | 0.1 | −20 | 100k | 100 |
|  | 0.1 |  |  | 100 | 1 | 10 | 20 | 1k | 60 |
|  | 1 |  |  |  |  | 1 | 0 | 10k | 80 |
|  | 10 |  |  |  |  | 0.1 | −20 | 100k | 100 |
|  | 100 |  |  |  |  | 0.01 | −40 | 1 Mega | 120 |

Bandpass filtering is one method used for parasitic rejection. The bandpass filter bandwidth is defined by two corner frequencies: the highpass and lowpass filter cut-off frequencies can be defined as, respectively, the low and high corner frequency of the bandpass filter. The highpass feature can also be used to attenuate the average DC and its drift in order to protect the electronic DC biasing.

Peripheral nerve recordings from LIFEs can be filtered from 300-600 Hz to 2.5-15 kHz (Malagodi, Horch et al. 1989; Goodall and Horch 1992; Yoshida and Horch 1996; Yoshida and Stein 1999; Dhillon, Lawrence et al. 2004). Usually, high-order highpass filters are used to attenuate the EMG signal while low-order lowpass filters are used to remove high-frequency noise. The EMG peak energy (about 250 Hz) explains the highpass filter cut-off frequency range, and high-order highpass filters can be used (respectively 5$^{th}$ and 8$^{th}$ order in (Yoshida and Horch 1996; Yoshida and Stein 1999) at 300 Hz and 600 Hz).

In an embodiment, the highpass and lowpass filter cut-off frequencies are defined between, respectively, 100-500 Hz and 5-10 kHz.

Providing a high common-mode gain is another method used for parasitic rejection. The CMRR is a result of the differential and common-mode gains.

An existing integrated recording circuit that uses an 85 dB-CMRR at 25 kHz for 74 dB amplification lead to approximately −10 dB of common mode amplification (Uranga, Navarro et al. 2004). Commercial recording systems usually provide a CMRR between 85 and 125 dB (CED 1902, CWE BMA-200, Grass Tech 15A12 DC/AC amplifier, as reviewed in (Uranga, Navarro et al. 2004)).

The final behavior of the common-mode rejection can be described as the system ability to attenuate the parasitic signal (e.g., EMG) while amplifying the signal-of-interest. The system could be then described as the attenuation of the output parasitic signal vs. the amplification of the signal- Digital Chopper-Modulated Recording Amplifiers The input-referred noise of chopper systems is often reported in terms of "average equivalent input white noise" since the Flicker noise has been suppressed by the chopper technique. For example, (Uranga, Navarro et al. 2004) reported an average equivalent input white noise of 6.6 nV/(Hz$^{1/2}$), which is equivalent to 361 nV$_{rms}$ if integrated on a 3 kHz-bandwidth, or 466 nV$_{rms}$ if integrated on a 5 kHz-bandwidth.

In an embodiment, the input-referred noise of a circuit or circuit system as described herein is no more than 1.25 $\mu V_{rms}$ on 5 kHz-bandwidth, which is equivalent to an average equivalent input white noise of 173 nV/(Hz$^{1/2}$). In a further embodiment, the input-referred noise of a circuit or circuit system as described herein is 1.25 $\mu V_{rms}$ on 5 kHz-bandwidth or about 1.25 $\mu V_{rms}$ on 5 kHz-bandwidth. In an alternative embodiment, the input-referred noise of a circuit or circuit system as described herein is no more than 1.25 $\mu V_{rms}$ on 3 kHz-bandwidth, which is equivalent to 22.8 nV/(Hz$^{1/2}$). In a further embodiment, the input-referred noise of a circuit or circuit system as described herein is 1.25 $\mu V_{rms}$ on 3 kEz-bandwidth or about 1.25 $\mu V_{rms}$ on 3 kHz-bandwidth.

The invention includes, but is not limited to, the following embodiments:

Embodiment 1

A circuit, comprising a low noise amplifier, wherein the low noise amplifier comprises an operational transconductance amplifier (OTA) having at least two differential input series-connected transistors (SCT).

Embodiment 2

The circuit according to embodiment 1, wherein the low noise amplifier is configured such that: the area per channel of the low noise amplifier is no more than 0.10 mm$^2$; the power consumption per channel of the low noise amplifier is no more than 200 μW; and the input-referred voltage noise density of the low noise amplifier is no more than 50 nV/(Hz$^{1/2}$) on 100 Hz-4 kHz bandwidth and no more than 30 nV/(Hz$^{1/2}$) on the main white Gaussian noise contribution over the full bandwidth.

Embodiment 3

The circuit according to embodiment 1, wherein the low noise amplifier is configured such that: the area per channel of the low noise amplifier is no more than 0.05 mm$^2$; the power consumption per channel of the low noise amplifier is no more than 20 μW; and the input-referred voltage noise density of the low noise amplifier is no more than 50 nV/(Hz$^{1/2}$) on 100 Hz-4 kHz bandwidth and no more than 30 nV/(Hz$^{1/2}$) on the main white Gaussian noise contribution over the full bandwidth.

Embodiment 4

The circuit according to any of embodiments 1-3, further comprising a highpass filter in operable communication with the low noise amplifier.

Embodiment 5

The circuit according to embodiment 4, wherein the highpass filter is configured to tune the bandwidth in a range of about 100 Hz and 500 Hz.

Embodiment 6

The circuit according to any of embodiments 4-5, wherein the highpass filter is a passive resistor-capacitor filter circuit.

Embodiment 7

The circuit according to any of embodiments 4-6, further comprising a discrete gain amplifier in operable communication with the highpass filter.

Embodiment 8

The circuit according to embodiment 7, wherein the discrete gain amplifier is a programmable discrete gain amplifier.

Embodiment 9

The circuit according to any of embodiments 1 or 4-8, wherein the low noise amplifier is configured such that: the area per channel of the low noise amplifier is no more than 0.10 mm$^2$; the power consumption per channel of the low noise amplifier is no more than 200 μW; and the input-referred voltage noise density of the low noise amplifier is no more than 50 nV/(Hz$^{1/2}$) on 100 Hz-4 kHz bandwidth and no more than 30 nV/(Hz$^{1/2}$) on the main white Gaussian noise contribution over the full bandwidth.

Embodiment 10

The circuit according to any of embodiments 1 or 4-8, wherein the implantable circuit is configured such that: the area per channel of the circuit is no more than 0.05 mm$^2$; the power consumption per channel of the circuit is no more than 20 μW; and the input-referred voltage noise density of the circuit is no more than 50 nV/(Hz$^{1/2}$) on 100 Hz-4 kHz bandwidth and no more than 30 nV/(Hz$^{1/2}$) on the main white Gaussian noise contribution over the full bandwidth.

Embodiment 11

The circuit according to any of embodiments 7-10, further comprising at least one processing circuit in operable communication with the discrete gain amplifier.

Embodiment 12

The circuit according to embodiment 11, wherein the at least one processing circuit comprises a comparator.

Embodiment 13

The circuit according to any of embodiments 11-12, wherein the discrete gain amplifier is configured to adapt a signal from the highpass filter to the dynamic input voltage/current range of the at least one processing circuit.

Embodiment 14

The circuit according to any of embodiments 1-13, wherein the circuit is configured to record low amplitude neural signals having an amplitude of less than 60 μV peak-to-peak.

Embodiment 15

The circuit according to any of embodiments 1-14, wherein the circuit is configured to reject signals with frequency components outside a tunable bandwidth.

Embodiment 16

The circuit according to embodiment 14, wherein a minimum frequency of the tunable bandwidth is 100 Hz, and wherein a maximum frequency of the tunable bandwidth is 10 kHz.

Embodiment 17

The circuit according to any of embodiments 1, 2, or 4-16, wherein the area per channel of the low noise amplifier is no more than 0.05 mm$^2$.

Embodiment 18

The circuit according to any of embodiments 1, 2, or 4-17, wherein the power consumption per channel of the low noise amplifier is no more than 20 μW.

Embodiment 19

The circuit according to any of embodiments 1-18, wherein the circuit is implantable (e.g., into a human subject).

Embodiment 20

A system for recording peripheral nerve activity, comprising:
the implantable circuit according to any of embodiments 1-19; and at least one electrode in operable communication with the implantable circuit.

Embodiment 21

The system according to embodiment 20, wherein the at least one electrode is a longitudinal intrafascicular electrode.

Embodiment 22

A method of recording peripheral nerve activity, comprising:
implanting at least one electrode in or on at least one peripheral nerve;
providing the implantable circuit according to any of embodiments 1-19 (or the system according to any of embodiments (20-21) in operable communication with the at least one electrode; and
recording activity of the at least one peripheral nerve using the implantable circuit.

Embodiment 23

The method according to embodiment 22, wherein the low noise amplifier of the implantable circuit is configured such that: the area per channel of the low noise amplifier is no more than 0.05 mm$^2$; the power consumption per channel of the low noise amplifier is no more than 20 μW; and the input-referred voltage noise density of the low noise amplifier is no more than 50 nV/(Hz$^{1/2}$) on 100 Hz-4 kHz bandwidth and no more than 30 nV/(Hz$^{1/2}$) on the main white Gaussian noise contribution over the full bandwidth.

Embodiment 24

An electronic circuit, wherein the circuit is configured to process neural activity to extract features,
wherein the circuit is configured such that: the area per channel of the circuit is no more than 0.10 mm$^2$; the power consumption per channel of the circuit is no more than 200 μW; and the input-referred voltage noise density of the circuit is no more than 50 nV/(Hz$^{1/2}$) on 100 Hz-4 kHz bandwidth and no more than 30 nV/(Hz$^{1/2}$) on the main white Gaussian noise contribution over the full bandwidth.

Embodiment 25

The electronic circuit according to embodiment 24, wherein the circuit is configured such that the area per channel of the circuit is no more than 0.05 mm$^2$.

Embodiment 26

The electronic circuit according to any of embodiments 24-25, wherein the circuit is configured such that the power consumption per channel of the circuit is no more than 20 μW.

Embodiment 27

The electronic circuit according to any of embodiments 24-25, wherein the circuit is configured such that the power consumption per channel of the circuit is no more than 150 μW.

Embodiment 28

The circuit according to any of embodiments 1, 2, 4-9, 10-17, or 19, wherein the power consumption per channel of the low noise amplifier is no more than 150 μW.

Embodiment 29

The circuit according to any of embodiments 1, 2, 4-9, 10-17, or 19, wherein the power consumption per channel of the circuit is no more than 150 μW.

Embodiment 30

The system according to any of embodiments 20-21, wherein the power consumption per channel of the low noise amplifier is no more than 150 μW.

Embodiment 31

The method according to embodiment 22, wherein the power consumption per channel of the low noise amplifier is no more than 150 μW.

Following are examples that illustrate procedures for practicing the invention. These examples should not be construed as limiting.

Example 1

There are two main types of hardware architectures for neural amplifiers that have been published: digital design based chopper-modulation amplifiers; and analog amplifiers. Published specifications of low noise amplifiers for peripheral nerve recording indicate that these specifications are not conducive to design of an implantable chip with acceptable power/area characteristics.

A circuit as shown in FIG. 4 was prepared using 0.18 μm complementary metal oxide semiconductor (CMOS) process. Characteristics of the circuit, including input-referred noise density, were measured and compared with characteristics of low noise amplifier systems used for recording. Table 2 shows the results, with the circuit of the subject invention shown on the first row of data.

Originally designed for brain recording, the best low noise amplifiers that could potentially be used for peripheral nerve recording are also presented in Table 2 (rows 2-8). They present acceptable power, noise, and/or size consumption considerations. However, an amplifier according to the subject invention allows equivalent noise performance for lower power and area consumption.

Figure 2:
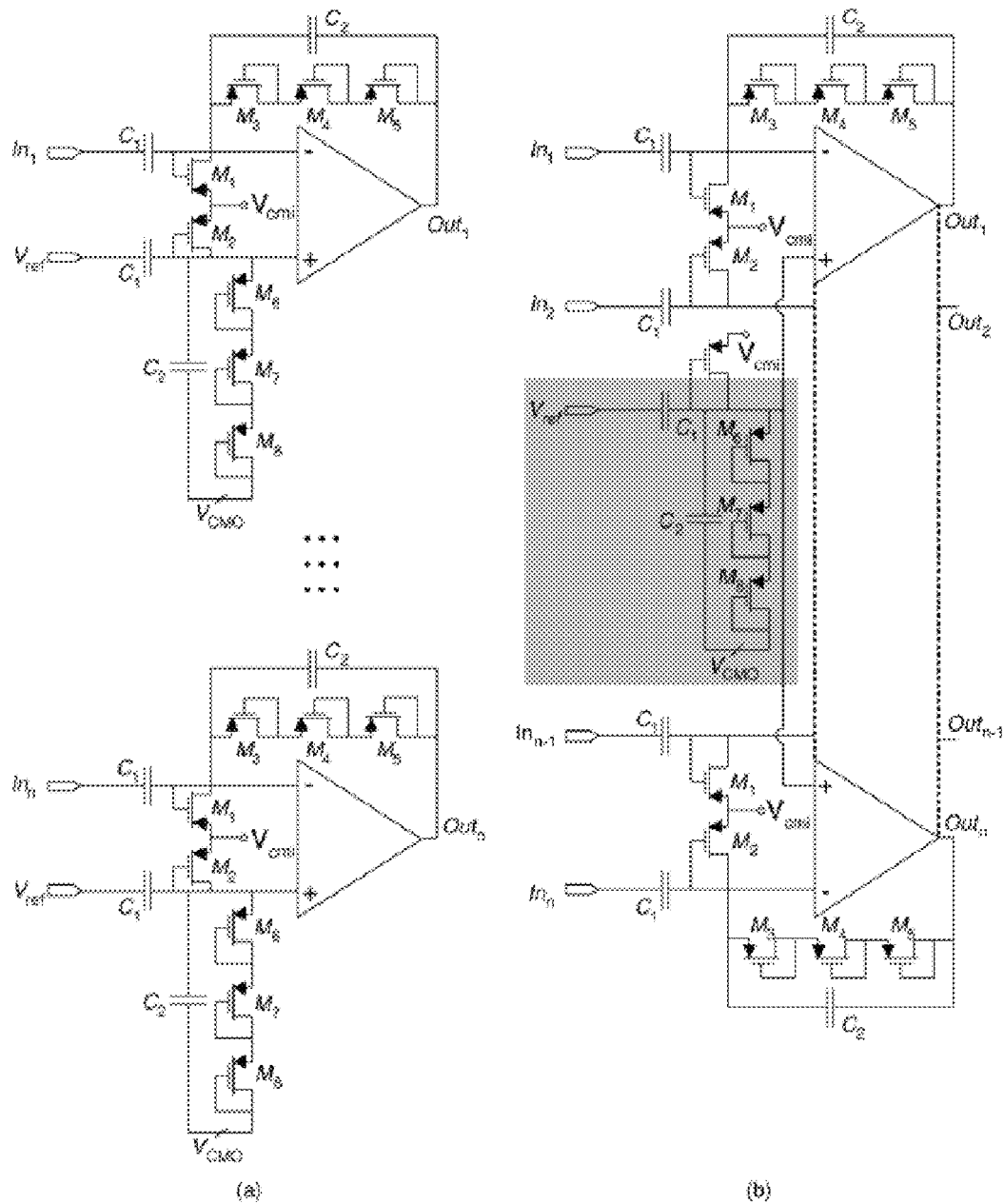
FIG. 2a shows a schematic of a shared operational transconductance amplifier (OTA) architecture.
FIG. 2b shows a schematic of a partial OTA sharing structure.
Figure 5:
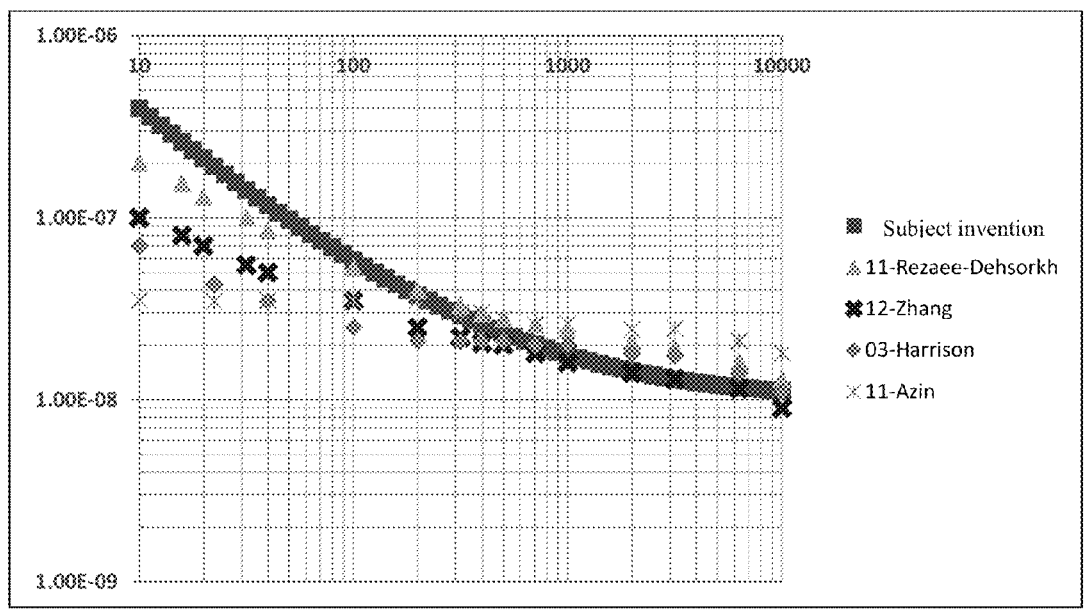
FIG. 5 shows a plot of input-referred voltage noise density versus frequency.

FIG. 5 shows a plot of the input-referred noise density comparison between the amplifier of the subject and the three best low noise amplifiers used for brain recording. Referring to FIG. 5, the y-axis is input-referred noise density (V/Hz$^{1/2}$), and the x-axis is frequency (Hz). The squares represent the circuit of the subject invention, the x's represent (Zhang, Hollerman et al. 2012), the triangles represent (Rezaee-Dehsorkh, Ravanshad et al. 2011), the diamonds represent (Harrison and Charles 2003), and the stars represent (Azin, Guggenmos et al. 2011). The bandwidth lowpass cut-off frequency of the overall recording system can be controlled with the additional amplifier (FIG. 2).

The circuit of the subject invention can also reach better noise performance by increasing the power consumption, with equivalent area consumption. Such a design is equivalent to the noise performance offered by (Uranga, Navarro et al. 2004) and (Rieger 2011) but has the advantage that it could be incorporated into an implantable chip and wirelessly powered (low power/area consumption).

and post-layout designs at room (27° C.) and body temperature (37° C.). A unique tunable voltage for low corner

TABLE 2

Latest low noise amplifier designs with the best noise performance

| Application | Design type | Circuit | Process (μm CMOS) | Input referred noise ($\mu V_{rms}$) | Integration bandwidth for Noise calculation | Amplification gain (dB) | Power consumption per channel (μW) | Area consumption ($mm^2$) | Amplifier filter bandwidth |
|---|---|---|---|---|---|---|---|---|---|
| Peripheral Nerve | Analog | Embodiment of the subject invention (3 shared channels) | 0.18 | 1.1 | 0.1-4 kHz | 40 | 32.5 | 0.05* | 80-100 kHz |
| | | (Limnuson, Tyler et al. 2009) | 1.5 | 1.95 | 0.3-6 kHz | 60 (full) | 1000 (full system) | 4.84* | (3 mHz)300 Hz-6 kHz |
| | | (Rieger 2011) | 0.35 | 1.84 | 0.1-10 kHz | 56 | 280 | 0.064 | 10-few kHz |
| | Digital | (Uranga, Navarro et al. 2004) | 0.7 | 0.45 | 3 kHz | 74 (full) | 965 for 1 LNA | 2.7* | N/A |
| Brain | Analog | (Zhang, Holleman et al. 2012) | 0.13 | 2.2 | 0.01 Hz-105 kHz | 40 | 12 | 0.072 | 0.05 Hz-10.5 kHz |
| | | (Rezaee-Dehsorkh, Ravanshad et al. 2011) | 0.18 | 2.38 | 0.5 Hz-50 kHz | 52-57 | 20.8 | 0.061 | 300 Hz-10 kHz |
| | | (Harrison and Charles 2003) | 1.5 | 2.2 | 0.5 Hz-50 kHz | 40 | 80 | 0.8 | 0.025 Hz-7.2 kHz |
| | | (Azin, Guggenmos et al. 2011) | 0.35 | 2.3 3.12 | 1.1-12k 0.5-50 kHz | 51.9-65.6 | 19.9-26.9 | 0.342 | (1.1-525)-(5.1k-12k) |
| | | (Lee, Lee et al. 2010) | 0.5 | 4.08 | 1-10k | 67.8-78 | 75 | N/A | N/A |
| | | (Wattanapanitch, Fee et al. 2007) | 0.5 | 3.06 | 45-5.3k | 40.8 | 7.56 | 0.16 | N/A |
| | | (Yin and Ghovanloo 2007) | 1.5 | 3.6 | 20-10 kHz | 39.3, 45.6 | 27.2 | 0.201 | (0.015-700)-(40, 400, 3k, 4k) |
| | | (Majidzadeh, Schmid et al. 2011) | 0.18 | 3.5 | 10-100k | 39.4 | 7.92 | 0.0625 | 10-7.2k |
| | | (Lopez, Prodanov et al. 2012) | 0.35 | 2.3-2.9 | 1 Hz-6 kHz | 40-75 | 231 | 0.97* approx | 572 Hz-6.2 kHz |
| | Digital | (Chen, Yang et al. 2011) | 0.18 | 0.9 | 10 kHz | 60.8 | 18 | 0.33 | 0.8 Hz-200/10 kHz |

Example 2

An implantable neural recording amplifier for use with longitudinal intrafascicular electrodes (LIFEs) was manufactured. It met the low noise and low power/area consumption specifications for low amplitude recordings.

The low noise architecture was similar to the design shown in FIG. 6 (Limunson, Tyler et al., 2009; Harrison and Charles, 2003) but the amplifier included an OTA and two SCTs as discussed herein. The C1 input capacitor provides an equivalent input impedance to the low noise amplifier several orders higher than the LIFE impedance (8 MΩ vs.~2-10 kΩ at 1 kHz). The low noise amplifier provides a tunable low corner frequency to allow rejection of EMG signals. The low noise amplifier area was 0.15 $mm^2$, designed with a 0.18 μm CMOS process. This design offers lower power/area consumption for equivalent noise performance of the integrated circuits for cuff recordings. The low noise amplifier meets low noise performance for ultra-low amplitude recording ability and low power/area consumption for a 16-channel recording system.

Figure 8:
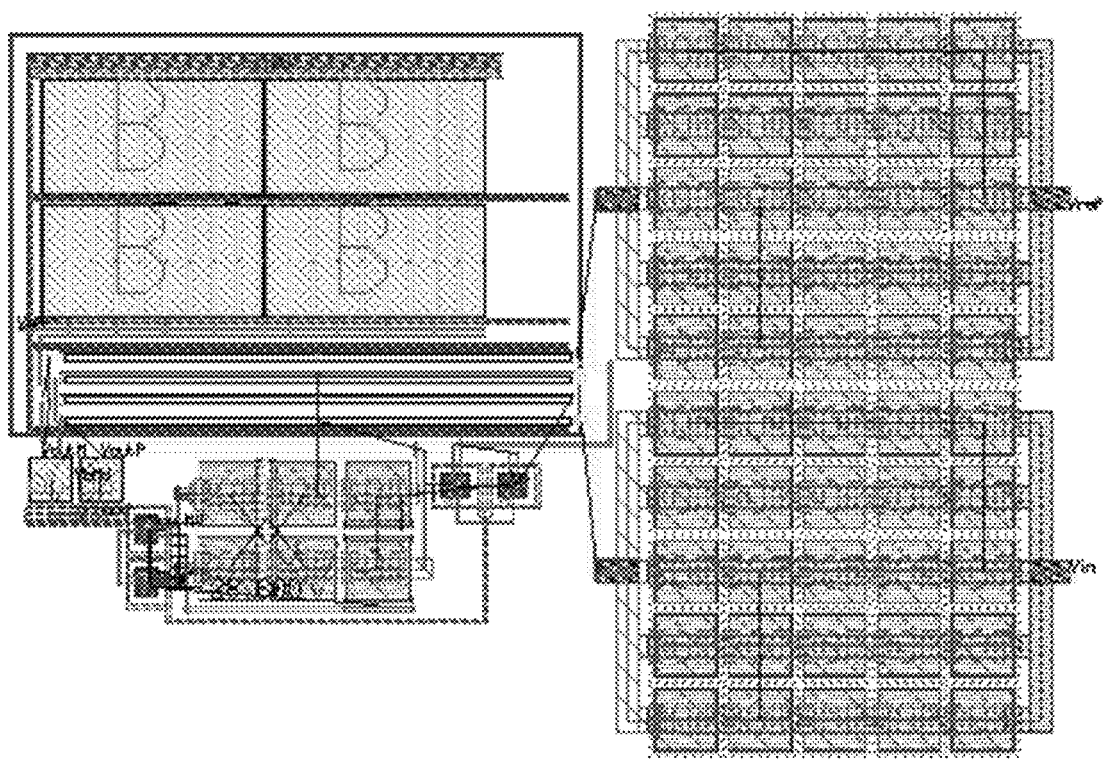
FIG. 8 shows a layout view of a circuit according to an embodiment of the subject invention.

The integrated circuit was designed using a TSMC 0.18 μm 1P2M CMOS process with a 1.0 femto-Farad (fF) metal-insulator-metal capacitor option. FIG. 8 shows a layout view for fabrication of the circuit for one channel.

The tuning sensitivity of the low corner frequency allows a wide range configuration (from a few Hertz to few kiloHertz) with a 650-850 mV range voltage control.

Monte Carlo simulations (mismatch and process) were performed for three design cases: the pre-layout schematic and post-layout designs at room (27° C.) and body temperature (37° C.). A unique tunable voltage for low corner frequency $f_{low}$ was set for all simulations (single post-layout simulation gives $f_{low}$=90.8 Hz). Selected Monte Carlo simulation runs in which the resultant $f_{low}$ was between 60 and 140 Hz are presented. This resultant $f_{low}$ range was chosen in order to remove the filter bandwidth variation impact on the input-referred noise performance; only the overall noise of the integrated components was evaluated. This selection will meet future noise measurement requirements and allow $f_{low}$ tuning capability. Table 3 shows a comparison of the amplifier of the subject invention with low noise amplifiers used with cuff electrodes for peripheral nerve recording. The input-referred noise was determined for the post-layout case (37° C.). The comparison amplifiers are those disclosed in (Limnuson, Tyler et al. 2009), abbreviated in Table 3 as "Limnuson 2009", and (Uranga, Navarro et al. 2004), abbreviated in Table 3 as "Uranga 2004".

Referring to Table 4, Monte Carlo simulations show that the low noise amplifier mid-gain, noise, and power performances are consistent between the pre-layout and post-layout designs based on the standard deviation of each parameter over the 155 iterations.

An additional gain amplifier may be required to relax input range performance of the analog signal processing circuits. There is no advantage in increasing the low noise amplifier mid-gain because it mainly relies on the C1 input capacitance (Harrison and Charles, 2003). Increasing the input capacitance will drastically increase the chip silicon area. Moreover, the increase in C1 leads to a decrease in the equivalent input impedance, which will divide the input signal circuit between the electrode equivalent capacitor and the low noise input impedance.

The low noise amplifier of the subject invention showed equivalent or better noise performance than those reported in the cuff-recording literature, and also had a power low enough (~200 µW/channel vs.~1 mW in the literature) to implement 16 recording channels in the integrated circuit (0.05 mm$^2$/channel). This low noise amplifier for ultra-low amplitude recording is also suitable for intrafascicular recordings from sensory fascicles since these have an equivalent signal amplitude range (Lefurge, Goodall et al., 1991; Malagodi, Horch et al., 1989).

Referring again to Table 4, the implantable amplifier achieved a mid-gain of 36.7±0.9% dB, input-referred noise of 2.3±7% µVrms on 10 Hz to 10 kHz at 37° C., and a power of 194±3%µW.

TABLE 3

Performance comparison with other Low noise amplifier designs for nerve recording

| Parameters | Subject Invention | Uranga 2004 | Limnuson 2009 |
|---|---|---|---|
| Amplifier Architecture | Analog | Chopper | Analog |
| Input-referred noise ($\mu V_{rms}$), (top) 0.3-3 kHz (bottom) 0.3-6 kHz | 0.7 ± 2.3%<br>0.6 ± 2.3% | 0.45<br>— | —<br>1.95 |
| Power (W) | 194µ | 1 m* | 965µ |
| Area (mm$^2$) | 0.15 | 2.7* | 4.8* |
| Process | 0.18 µm | 0.7 µm | 1.5 µm |

*Performance reported for the full recording system, including additional filter and amplification circuits, and/or analog signal processing circuits.

TABLE 4

Monte Carlo simulated performances*

| Parameters | Pre-Layout (27° C.) | Post-Layout (27° C.) | Post-Layout (37° C.) |
|---|---|---|---|
| Mid-Gain (dB) | 37.3 ± 0.9% | 36.7 ± 0.9% | 36.7 ± 0.9% |
| Low corner frequency (Hz) | 91.1 ± 24% | 75.1 ± 12% | 116 ± 12% |
| Input referred noise on 10 Hz-10 kHz ($\mu V_{rms}$) | 2.0 ± 11% | 1.9 ± 6% | 2.3 ± 7% |
| Power (µW) | 203 ± 3% | 203 ± 3% | 194 ± 3% |

*Selected Monte Carlo simulation (155 iterations) with the low corner frequency in 60-140 Hz. Mean and standard deviation are reported All patents, patent applications, provisional applications, and publications referred to or cited herein (including those listed in the References section) are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

Arnaud, A., R. Fiorelli, et al. (2006). "Nanowatt, Sub-nS OTAs, With Sub-10-mV Input Offset, Using Series-Parallel Current Mirrors." *Solid-State Circuits, IEEE Journal of* 41(9): 2009-2018.

Azin, M., D. J. Guggenmos, et al. (2011). "A Battery-Powered Activity-Dependent Intracortical Microstimulation IC for Brain-Machine-Brain Interface." *Solid-State Circuits, IEEE Journal of* 46(4): 731-745.

Branner, A. and R. A. Normann (2000). "A multielectrode array for intrafascicular recording and stimulation in sciatic nerve of cats." *Brain Res Bull* 51(4): 293-306.

Branner, A., R. B. Stein, et al. (2004). "Long-term stimulation and recording with a penetrating microelectrode array in cat sciatic nerve." *IEEE Trans Biomed Eng* 51(1): 146-157.

Campbell, P. K., K. E. Jones, et al. (1991). "A silicon-based, three-dimensional neural interface: manufacturing processes for an intracortical electrode array." *IEEE Trans Biomed Eng* 38(8): 758-768.

Chen, W.-M., W.-C. Yang, et al. (2011). *The design of CMOS general-purpose analog front-end circuit with tunable gain and bandwidth for biopotential signal recording systems.* Engineering in Medicine and Biology Society, EMBC, 2011 Annual International Conference of the IEEE.

Dagtekin, M., L. Wentai, et al. (2001). *A multi channel chopper modulated neural recording system.* Engineering in Medicine and Biology Society, 2001. Proceedings of the 23rd Annual International Conference of the IEEE.

Denison, T., K. Consoer, et al. (2007). "A 2 uW 100 nV/rtHz Chopper-Stabilized Instrumentation Amplifier for Chronic Measurement of Neural Field Potentials." *Solid-State Circuits, IEEE Journal of* 42(12): 2934-2945.

Dhillon, G. S. and K. W. Horch (2005). "Direct neural sensory feedback and control of a prosthetic arm." *IEEE Trans Neural Syst Rehabil Eng* 13(4): 468-472.

Dhillon, G. S., T. B. Kruger, et al. (2005). "Effects of short-term training on sensory and motor function in severed nerves of long-term human amputees." *J Neurophysiol* 93(5): 2625-2633.

Dhillon, G. S., S. M. Lawrence, et al. (2004). "Residual function in peripheral nerve stumps of amputees: implications for neural control of artificial limbs." *J Hand Surg [Am]* 29(4): 605-615; discussion 616-608.

Dhillon, G. S., S. M. Lawrence, et al. (2004). "Residual function in peripheral nerve stumps of amputees: implications for neural control of artificial limbs." *J Hand Surg Am* 29(4): 605-615; discussion 616-608.

Edell, D. J. (1986). "A peripheral nerve information transducer for amputees: long-term multichannel recordings from rabbit peripheral nerves." *IEEE Trans Biomed Eng* 33(2): 203-214.

Figoni, S. F., R. M. Glaser, et al. (1991). "Acute hemodynamic responses of spinal cord injured individuals to functional neuromuscular stimulation-induced knee extension exercise." *J Rehabil Res Dev* 28(4): 9-18.

Gibson, S., J. W. Judy, et al. (2010). "Technology-Aware Algorithm Design for Neural Spike Detection, Feature Extraction, and Dimensionality Reduction." *Neural Systems and Rehabilitation Engineering, IEEE Transactions on* 18(5): 469-478.

Goodall, E., T. Lefurge, et al. (1991). "Information contained in sensory nerve recordings made with intrafascicular electrodes." *IEEE Trans. Biomed. Eng.* 38: 846-850.

Goodall, E. V. and K. W. Horch (1992). "Separation of action potentials in multiunit intrafascicular recordings." *IEEE Trans Biomed Eng* 39(3): 289-295.

Goodall, E. V., T. M. Lefurge, et al. (1991). "Information contained in sensory nerve recordings made with intrafascicular electrodes." *Biomedical Engineering, IEEE Transactions on* 38(9): 846-850.

Grill, W. M. (2000). "Electrical activation of spinal neural circuits: Application to motor-system neural prostheses." *Neuromodulation* 3: 97-106.

Hallin, R. G. (1990). "Microneurography in relation to intraneural topography: somatotopic organisation of median nerve fascicles in humans." *J Neurol Neurosurg Psychiatry* 53(9): 736-744.

Hallin, R. G. and G. Wu (2001). "Fitting pieces in the peripheral nerve puzzle." *Exp Neurol* 172(2): 482-492.

Harrison, R. R. (2008). "The Design of Integrated Circuits to Observe Brain Activity," Proceedings of the IEEE, Vol. 96, No. 7, pp. 1203-1216.

Harrison, R. R. and C. Charles (2003). "A low-power low-noise CMOS amplifier for neural recording applications." *Solid-State Circuits, IEEE Journal of* 38(6): 958-965.

Jensen, W., T. Sinkjaer, et al. (2002). "Improving signal reliability for on-line joint angle estimation from nerve cuff recordings of muscle afferents." *IEEE Trans Neural Syst Rehabil Eng* 10(3): 133-139.

Keith, M. W. (2001). "Neuroprostheses for the upper extremity." *Microsurgery* 21(6): 256-263.

Kovacs, G. T., C. W. Storment, et al. (1992). "Regeneration microelectrode array for peripheral nerve recording and stimulation." *IEEE Trans Biomed Eng* 39(9): 893-902.

Kyung Hwan, K. and K. Sung June (2000). "Neural spike sorting under nearly 0-dB signal-to-noise ratio using nonlinear energy operator and artificial neural-network classifier." *Biomedical Engineering, IEEE Transactions on* 47(10): 1406-1411.

Lee, J., M. D. Johnson, et al. (2010). "A Tunable Biquad Switched-Capacitor Amplifier-Filter for Neural Recording." *Biomedical Circuits and Systems, IEEE Transactions on* 4(5): 295-300.

Lee, S. B., H.-M. Lee, et al. (2010). "An Inductively Powered Scalable 32-Channel Wireless Neural Recording System-on-a-Chip for Neuroscience Applications." *Biomedical Circuits and Systems, IEEE Transactions on* 4(6): 360-371.

Lefurge, T., E. Goodall, et al. (1991). "Chronically implanted intrafascicular recording electrodes." *Ann Biomed Eng* 19(2): 197-207.

Limnuson, K., D. J. Tyler, et al. (2009). *Integrated electronics for peripheral nerve recording and signal processing*. Engineering in Medicine and Biology Society, 2009. EMBC 2009. Annual International Conference of the IEEE.

Lopez, C. M., D. Prodanov, et al. (2012). "A Multichannel Integrated Circuit for Electrical Recording of Neural Activity, With Independent Channel Programmability." *Biomedical Circuits and Systems, IEEE Transactions on* 6(2): 101-110.

Majidzadeh, V., A. Schmid, et al. (2011). "Energy Efficient Low-Noise Neural Recording Amplifier With Enhanced Noise Efficiency Factor." *Biomedical Circuits and Systems, IEEE Transactions on* 5(3): 262-271.

Malagodi, M. S., K. W. Horch, et al. (1989). "An intrafascicular electrode for recording of action potentials in peripheral nerves." *Ann Biomed Eng* 17(4): 397-410.

Malmstrom, J. A., T. G. McNaughton, et al. (1998). "Recording properties and biocompatibility of chronically implanted polymer-based intrafascicular electrodes." *Ann Biomed Eng* 26(6): 1055-1064.

McDonnall, D., G. A. Clark, et al. (2004). "Selective motor unit recruitment via intrafascicular multielectrode stimulation." *Can. J. Physiol. Pharmacol.* 82: 599-609.

McNaughton, T. G. and K. W. Horch (1994). "Action potential classification with dual channel intrafascicular electrodes." *IEEE Trans Biomed Eng* 41(7): 609-616.

Mensinger, A. F., D. J. Anderson, et al. (2000). "Chronic recording of regenerating VIIIth nerve axons with a sieve electrode." *J Neurophysiol* 83(1): 611-615.

Nabar, N. and K. Rajgopal (2009). *A wavelet based Teager energy operator for spike detection in microelectrode array recordings*. TENCON 2009-2009 IEEE Region 10 Conference.

Naples, G. G., J. T. Mortimer, et al. (1988). "A spiral nerve cuff electrode for peripheral nerve stimulation." *IEEE Trans Biomed Eng* 35(11): 905-916.

Navarro, X., E. Valderrama, et al. (2001). "Selective fascicular stimulation of the rat sciatic nerve with multipolar polyimide cuff electrodes." *Restor Neurol Neurosci* 18(1): 9-21.

Nikolic, Z. M., D. B. Popovic, et al. (1994). "Instrumentation for ENG and EMG recordings in FES systems." *Biomedical Engineering, IEEE Transactions on* 41(7): 703-706.

Obeid, I. (2007). *Comparison of Spike Detectors based on Simultaneous Intracellular and Extracellular Recordings*. Neural Engineering, 2007. CNE '07. 3rd International IEEE/EMBS Conference on.

Obeid, I. and P. D. Wolf (2004). "Evaluation of spike-detection algorithms for a brain-machine interface application." *Biomedical Engineering, IEEE Transactions on* 51(6): 905-911.

Ohnishi, K., Weir, R. F. et al. (2007). "Neural machine interfaces for controlling multifunctional powered upper-limb prostheses," *Expert Rvv Med Devices*, vol. 4, pp. 43-53.

Razavi (2003). "Design of Analog CMOS Integrated Circuits."

Rezaee-Dehsorkh, H., N. Ravanshad, et al. (2011). "Analysis and Design of Tunable Amplifiers for Implantable Neural Recording Applications." *Emerging and Selected Topics in Circuits and Systems, IEEE Journal on* 1(4): 546-556.

Rieger, R. (2011). "Variable-Gain, Low-Noise Amplification for Sampling Front Ends." *Biomedical Circuits and Systems, IEEE Transactions on* 5(3): 253-261.

Rossini, P. M., J. Rigosa, et al. (2011). "Stump nerve signals during transcranial magnetic motor cortex stimulation recorded in an amputee via longitudinal intrafascicular electrodes." *Exp Brain Res* 210(1): 1-11.

Shalchyan, V., W. Jensen, et al. (2012). "Spike Detection and Clustering With Unsupervised Wavelet Optimization in Extracellular Neural Recordings." *Biomedical Engineering, IEEE Transactions on* 59(9): 2576-2585.

Stein, R. B., D. Charles, et al. (1975). "Principles underlying new methods for chronic neural recording." *Can J Neurol Sci* 2(3): 235-244.

Stein, R. B., T. R. Nichols, et al. (1977). "Stable long-term recordings from cat peripheral nerves." *Brain Res* 128(1): 21-38.

Sweeney, J. D., N. R. Crawford, et al. (1995). "Neuromuscular stimulation selectivity of multiple-contact nerve cuff electrode arrays." *Med Biol Eng Comput* 33(3 Spec No): 418-425.

Upshaw, B. and T. Sinkjaer (1998). "Digital signal processing algorithms for the detection of afferent nerve activity recorded from cuff electrodes." *Rehabilitation Engineering, IEEE Transactions on* 6(2): 172-181.

Uranga, A., X. Navarro, et al. (2004). "Integrated CMOS amplifier for ENG signal recording." *Biomedical Engineering, IEEE Transactions on* 51(12): 2188-2194.

Venkatasubramanian, G., R. Jung, et al. (2006). Functional Electrical Stimulation. *The Wiley Encyclopedia of Medical Devices and Instrumentation.* J. G. Webster, Wiley-Interscience.

Watchmaker, G., C. Gumucio, et al. (1991). "Fascicular topography of the median nerve: a computer based study to identify branching patterns." *J Hand Surg [Am]* 16A: 53-59.

Wattanapanitch, W., M. Fee, et al. (2007). "An Energy-Efficient Micropower Neural Recording Amplifier." *Biomedical Circuits and Systems, IEEE Transactions on* 1(2): 136-147.

Xu, J., R. F. Yazicioglu, et al. (2011). "A 160 uW 8-Channel Active Electrode System for EEG Monitoring." *Biomedical Circuits and Systems, IEEE Transactions on* 5(6): 555-567.

Yazicioglu, R. F., P. Merken, et al. (2006). *A 60 uW 60 nV/Hz Readout Front-End for Portable Biopotential Acquisition Systems.* Solid-State Circuits Conference, 2006. ISSCC 2006. Digest of Technical Papers. IEEE International.

Yin, M. and M. Ghovanloo (2007). *A Low-Noise Preamplifier with Adjustable Gain and Bandwidth for Biopotential Recording Applications.* Circuits and Systems, 2007. ISCAS 2007. IEEE International Symposium on.

Yoshida, K. and K. Horch (1996). "Closed-loop control of ankle position using muscle afferent feedback with functional neuromuscular stimulation." *Biomedical Engineering, IEEE Transactions on* 43(2): 167-176.

Yoshida, K. and R. Riso (2004). Peripheral nerve recording electrodes and techniques. *Neuroprosthetics: Theory and Practice.* K. W. Horch and G. S. Dhillon, World Scientific.

Yoshida, K. and R. B. Stein (1999). "Characterization of signals and noise rejection with bipolar longitudinal intrafascicular electrodes." *IEEE Trans Biomed Eng* 46(2): 226-234.

Zhang, F., J. Holleman, et al. (2012). "Design of Ultra-Low Power Biopotential Amplifiers for Biosignal Acquisition Applications." *Biomedical Circuits and Systems, IEEE Transactions on* 6(4): 344-355.

Zheng, X., J. Zhang, et al. (2003). "Longitudinally implanted intrafascicular electrodes for stimulating and recording fascicular physioelectrical signals in the sciatic nerve of rabbits."*Microsurgery* 23(3): 268-273.

Ziel, A. V. D. (1970). *Noise: sources, characterization, measurement.*

Zumsteg, Z. S., C. Kemere, et al. (2005). "Power feasibility of implantable digital spike sorting circuits for neural prosthetic systems." *Neural Systems and Rehabilitation Engineering, IEEE Transactions on* 13(3): 272-279.

What is claimed is:

1. An implantable circuit, comprising a low noise amplifier, the low noise amplifier comprising an operational transconductance amplifier (OTA) having at least two differential input series-connected transistors (SCT), each differential input SCT including an input terminal that is directly connected to the input terminal of each other differential input SCT, the input terminal of each differential input SCT being connected to the same differential input of the OTA, and the at least two differential input SCTs being connected to each other such that the entire current flowing through each differential input SCT flows into every other differential input SCT.

2. The implantable circuit according to claim 1, wherein the low noise amplifier is configured such that: the area per channel of the low noise amplifier is no more than 0.05 mm$^2$; the power consumption per channel of the low noise amplifier is more than 0 μW and no more than 150 μW; and the input-referred voltage noise density of the circuit is more than 0 nV/(Hz$^{1/2}$) and no more than 50 nV/(Hz$^{1/2}$) on 100 Hz-4 kHz bandwidth and more than 0 nV/(Hz$^{1/2}$) and no more than 30 nV/(Hz$^{1/2}$) on the main white Gaussian noise contribution over the full bandwidth.

3. The implantable circuit according to claim 1, further comprising a highpass filter in operable communication with the low noise amplifier.

4. The implantable circuit according to claim 3, wherein the highpass filter is configured to tune the bandwidth in a range of about 100 Hz and 500 Hz.

5. The implantable circuit according to claim 3, wherein the highpass filter is a passive resistor-capacitor filter circuit.

6. The implantable circuit according to claim 3, further comprising a discrete gain amplifier in operable communication with the highpass filter.

7. The implantable circuit according to claim 6, wherein the discrete gain amplifier is a programmable discrete gain amplifier.

8. The implantable circuit according to claim 6, wherein the implantable circuit is configured such that: the area per channel of the circuit is no more than 0.05 mm$^2$; the power consumption per channel of the circuit is more than 0 μW and no more than 150 μW; and the input-referred voltage noise density of the circuit is more than 0 nV/(Hz$^{1/2}$) and no more than 50 nV/(Hz$^{1/2}$) on 100 Hz-4 kHz bandwidth and more than 0 nV/(Hz$^{1/2}$) and no more than 30 nV/(Hz$^{1/2}$) on the main white Gaussian noise contribution over the full bandwidth.

9. The implantable circuit according to claim 6, further comprising at least one processing circuit in operable communication with the discrete gain amplifier.

10. The implantable circuit according to claim 9, wherein the at least one processing circuit comprises a comparator.

11. The implantable circuit according to claim 9, wherein the discrete gain amplifier is configured to adapt a signal from the highpass filter to the dynamic input voltage/current range of the at least one processing circuit.

12. The implantable circuit according to claim 1, wherein the circuit is configured to record low amplitude neural signals having an amplitude of less than 60 μV peak-to-peak.

13. The implantable circuit according to claim 12, wherein the circuit is configured to reject signals with frequency components outside a tunable bandwidth.

14. The implantable circuit according to claim 13, wherein a minimum frequency of the tunable bandwidth is 100 Hz, and wherein a maximum frequency of the tunable bandwidth is 10 kHz.

15. The implantable circuit according to claim 14, wherein the area per channel of the low noise amplifier is no more than 0.05 mm$^2$.

16. A system for recording peripheral nerve activity, comprising:
the implantable circuit according to claim 1; and
at least one electrode in operable communication with the implantable circuit.

17. The system according to claim 16, wherein the at least one electrode is a longitudinal intrafascicular electrode.

18. An implantable circuit, comprising:
a low noise amplifier;
a highpass filter in operable communication with the low noise amplifier;
a discrete gain amplifier in operable communication with the highpass filter; and
at least one processing circuit in operable communication with the discrete gain amplifier, the low noise amplifier comprising an operational transconductance amplifier (OTA) having at least two differential input series-connected transistors (SCT), each input differential SCT including an input terminal that is directly connected to the input terminal of each other differential input SCT, each differential input SCT being connected to the same differential input of the OTA, and the at least two differential input SCI's being connected to each other such that the entire current flowing through each differential input SCT flows into every other differential input SCT, and the implantable circuit being configured such that: the area per channel of the circuit is no more than 0.05 mm$^2$; the power consumption per channel of the circuit is more than 0 μW and no more than 150 μW; and the input-referred voltage noise density of the circuit is more than 0 nV/(Hz$^{1/2}$) and no more than 50 nV/(Hz$^{1/2}$) on 100 Hz-4 kHz bandwidth and more than 0 nV/(Hz$^{1/2}$) and no more than 30 nV/(Hz$^{1/2}$) on the main white Gaussian noise contribution over the full bandwidth.

19. The implantable circuit according to claim 18, wherein the highpass filter is configured to tune the bandwidth in a range of about 100 Hz and 500 Hz, wherein the highpass filter is a passive resistor-capacitor filter circuit, wherein the discrete gain amplifier is a programmable discrete gain amplifier, wherein the at least one processing circuit comprises a comparator, wherein the discrete gain amplifier is configured to adapt a signal from the highpass filter to the dynamic input voltage/current range of the at least one processing circuit, wherein the circuit is configured to record low amplitude neural signals having an amplitude of less than 60 μV peak-to-peak, wherein the circuit is configured to reject signals with frequency components outside a tunable bandwidth, wherein a minimum frequency of the tunable bandwidth is 100 Hz, and wherein a maximum frequency of the tunable bandwidth is 10 kHz, and wherein the area per channel of the low noise amplifier is no more than 0.05 mm$^2$.

20. A system for recording peripheral nerve activity, comprising:

the implantable circuit according to claim 18; and at least one electrode in operable communication with the implantable circuit.

21. An implantable circuit, comprising a low noise amplifier, the low noise amplifier comprising:

an operational transconductance amplifier (OTA) having a first reference input, a first reference output, a first input, and a first output;

a first resistor and a first capacitor connected between the first reference input of the OTA and the first reference output of the OTA; and a second resistor and a second capacitor connected between the first input of the OTA and the first output of the OTA, the OTA comprising:

a first branch series-connected transistor (SCT) connected to the first reference input of the OTA; and a second branch SCT connected to the first input of the OTA, the first branch SCT having at least two first branch transistors, and the second branch SCT having at least two second branch transistors.

22. The implantable circuit according to claim 21, wherein each first branch transistor comprises an input terminal that is directly connected to the input terminal of each other first branch transistor and directly connected to the first reference input of the OTA, and wherein each second branch transistor comprises an input terminal that is directly connected to the input terminal of each other second branch transistor and directly connected to the first input of the OTA.

23. The implantable circuit according to claim 22, wherein the first branch transistors include a first PMOS first branch transistor and a second PMOS first branch transistor, wherein a drain of the first PMOS first branch transistor is connected to a source of the second PMOS first branch transistor, wherein a gate of the first PMOS first branch transistor and a gate of the second PMOS first branch transistor are directly connected to each other, wherein the second branch transistors include a first PMOS second branch transistor and a second PMOS second branch transistor, wherein a drain of the first PMOS second branch transistor is connected to a source of the second PMOS second branch transistor, and wherein a gate of the first PMOS second branch transistor and a gate of the second PMOS second branch transistor are directly connected to each other.

* * * * *

UNITED STATES PATENT AND TRADEMARK OFFICE
CERTIFICATE OF CORRECTION

PATENT NO. : 9,662,025 B2
APPLICATION NO. : 13/886934
DATED : May 30, 2017
INVENTOR(S) : Adeline Zbrzeski et al.

Page 1 of 1

It is certified that error appears in the above-identified patent and that said Letters Patent is hereby corrected as shown below:

In the Specification

Column 1, Lines 5-8:
"This invention was made with government support under a grant awarded from the National Institute of Health (NIH) under grant number NIH-R01EB008578. The government has certain rights in this invention."

Should read:
-- This invention was made with government support under EB008578 awarded by the National Institutes of Health. The government has certain rights in the invention. --

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*